United States Patent
Imai et al.

(10) Patent No.: US 6,708,119 B2
(45) Date of Patent: Mar. 16, 2004

(54) METHOD AND APPARATUS FOR AUTOMATICALLY REMOVING VECTOR UNIT IN DNA BASE SEQUENCE

(75) Inventors: Kensaku Imai, Kawasaki (JP); Masato Kitajima, Fukuoka (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/785,269

(22) Filed: Feb. 20, 2001

(65) Prior Publication Data

US 2002/0018736 A1 Feb. 14, 2002

Related U.S. Application Data

(63) Continuation of application No. 08/684,674, filed on Jul. 22, 1996, now abandoned.

(30) Foreign Application Priority Data

Jul. 27, 1995 (JP) .............................................. 7-192005

(51) Int. Cl.[7] .............................................. G06F 19/00
(52) U.S. Cl. ....................................................... 702/20
(58) Field of Search ........................................... 702/20

(56) References Cited

PUBLICATIONS

Smith et al, High Throughput DNA Sequencing Using an Automated Electrophoresis Analysis System and a Novel Sequence Assembly Program, 1993, BioTechniques, vol. 14, No. 6, pp. 1014–1018.*

Smith, et al., "High Throughput DNA Sequencing Using an . . . Sequence Assembly Program", *Biotechniques*, vol. 14, No. 6 (1993) pp. 1014–1018.

R. Staden, "Automation of the Computer Handling . . . DNA Sequencing", *Nucleic Acids Research*, vol. 10, No. 15 (1982) pp. 4731–4751.

U.S. patent application Ser. No. 08/684,674, Imai et al., filed Jun. 22, 1996.

* cited by examiner

*Primary Examiner*—John S. Brusca
(74) *Attorney, Agent, or Firm*—Staas & Halsey LLP

(57) ABSTRACT

An automatic DNA fragment removing method aims at removing a vector unit base sequence, that is, a base sequence in a portion of a vector, with precision from the DNA integrated into the vector and processed in a cloning process, so as to obtain a target DNA fragment in an exact structure. Depending on the vector and the restriction enzyme used for cleaving the vector and generating an object DNA fragment, a retrieval key is generated to retrieve a vector unit from the DNA base sequence obtained as the cloning process. Using the generated retrieval key, the junction between the DNA fragment and the vector unit is specified, and the specified junction and the base sequence outside the junction are automatically removed as the vector unit.

9 Claims, 25 Drawing Sheets

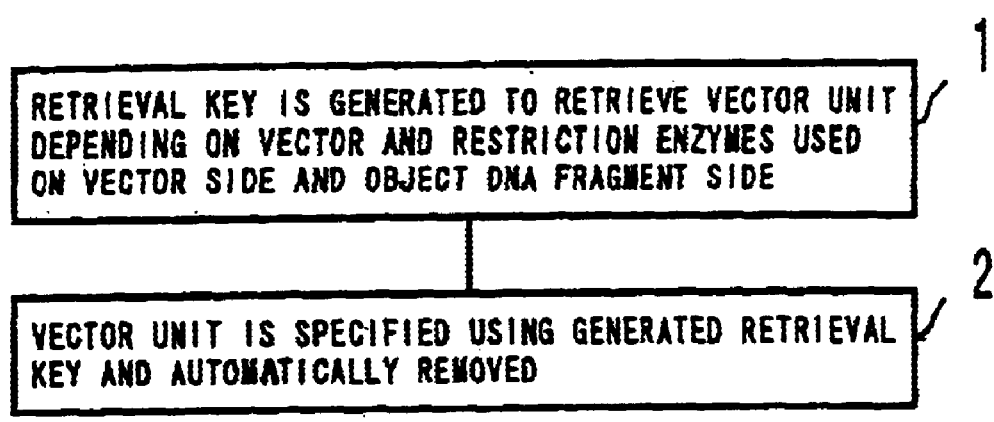
F I G. 5

```
M13MP18
M13MP19
PBR322
PSL1180
PSL1190
PT7T318U
PT7T319U
PTZ18R
PTZ19R
PUC18
PUC19, ETC.
```

FIG. 8

```
VECTOR DB FORMAT

>ID
PUC18
>SEQ ID: 11
TCGCGCGTTTCGGTGATGACGGTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGGCTGGCTTAACTATGCGGCATCAGA
GCAGATTGTACTGAGAGTGCACCATATGCGGTGTGAAATACCGCACAGATGCGTAAGGAGAAAATACCGCATCAGGCGCC
ATTCGCCATTCAGGCTGCGCAACTGTTGGGAAGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGTCACGACGTTGTAAAACGACGGCCAGTGCCAA
GCTTGCATGCCTGCAGGTCGACTCTAGAGGATCCCCGGGTACCGAGCTCGAATTCGTAATCATGGTCATAGCTGTTTCCT
GTGTGAAATTGTTATCCGCTCACAATTCCACACAACATACGAGCCGGAAGCATAAAGTGTAAAGCCTGGGGTGCCTAATG
AGTGAGCTAACTCACATTAATTGCGTTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTTCCTCGCTCACTGACTCGCTGCGCTCG
GTCGTTCGGCTGCGGCGAGCGGTATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTGTCCGCCTTTCTCCCTTC
GGGAAGCGTGGCGCTTTCTCAAAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGCGGTGCTACAGAGTTCTTGAAGTG
GTGGCCTAACTACGGCTACACTAGAAGAACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCGATCTGTCTATTTCGTTCA
TCCATAGTTGCCTGACTCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTTTGGTATGGCTTCATTCAGCTCCGGTTCCCA
ACGATCAAGGCGAGTTACATGATCCCCCATGTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTTCTTCGGGGCGAAAACTCT
CAAGGATCTTACCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAAATGTTGAAT
ACTCATACTCTTCCTTTTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTGACGTCTAAGAAACCATTATTATC
ATGACATTAACCTATAAAAATAGGCGTATCACGAGGCCCTTTCGTC
>MULTI
399..450
```

FIG. 9

( * INDICATES MULTIPLE CLONING SITE )

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

SEQ ID: 12    GTGCCAAGCTTGCATGCCTGCAGGTCGACTCTAGAGGATCCCCGGGTACCGAGCTCGAATTCGTAAT

SEQ ID: 13   AAGCTT ⇔ HIND III

SEQ ID: 14   GCATGC ⇔ SPH I

SEQ ID: 15   CTGCAG ⇔ PST I

SEQ ID: 16   GTCGAC ⇔ SAL I, ACC I, HINC II

SEQ ID: 17   TCTAGA ⇔ XBA I

SEQ ID: 18   GGATCC ⇔ BAMH I

SEQ ID: 19   CCCGGG ⇔ SMA I, XMA I

SEQ ID: 20   GGTACC ⇔ KPN I

SEQ ID: 21   GAGCTC ⇔ SAC I

SEQ ID: 22   GAATTC ⇔ ECOR I

FIG. 10

| VECTOR SIDE | OBJECT DNA FRAGMENT SIDE |
|---|---|
| HIND III | HINDIII |
| SPH I | SPH I |
| PST I | PST I |
| SAL I | SAL I |
| ACC I | ACC I |
| HINC II | HINC II |
| XBA I | XBA I |
| BAMH I | BAMH I |
| SMA I | SMA I |
| XMA I | XMA I |
| KPN I | KPN I |
| SAC I | SAC I |
| ECOR I | ECOR I |
|  | OTHER RESTRICTION ENZYME |
|  | ... |

FIG. 11

S21 — DETERMINING RETRIEVAL KEY

TWO RETRIEVAL KEYS ARE GENERATED ON EACH OF 5' (FORWARD) AND 3' (BACKWARD) SIDES ACCORDING TO VECTOR TYPE AND RESTRICTION ENZYME INFORMATION

⇩

S22 — HOMOLOGY RETRIEVAL

AFTER HOMOLOGY RETRIEVAL USING RETRIEVAL KEY, PRIMARY CANDIDATE LISTS FOR BOUNDARY PORTION 5' AND 3' SIDES ARE GENERATED

⇩

S23 — HOMOLOGY CHECK

HOMOLOGY CHECK IS MADE BETWEEN MUTIPLE CLONING SITE AND PRECEDING AREA OF PRIMARY CANDIDATE FOR 5' BOUNDARY PORTION AND FOLLOWING AREA OF PRIMARY CANDIDATE FOR 3' BOUNDARY PORTION TO GENERATE LIST OF SECONDARY CANDIDATES FOR BOUNDARY PORTION

⇩

S24 — SPECIFYING BOUNDARY AREA

CHECK THAT EACH CANDIDATE IS UNIQUE, AND CHECK POSITIONAL RELATIONSHIP BETWEEN 5' SIDE SECONDARY CANDIDATE AND 3' SIDE SECONDARY CANDIDATE. IF OK, THESE CANDIDATES ARE SPECIFIED AS VECTOR UNIT.

⇩

S25 — DETERMINING PORTION CLEAVED

PORTION CLEAVED IN BOUNDARY AREA IS DETERMINED

F I G. 1 2

FIG. 13A WHEN SINGLE-STRANDED AREA IS FOUND ON 3' SIDE

FIG. 13B WHEN NO SINGLE-STRANDED AREA IS FOUND

FIG. 13C WHEN SINGLE-STRANDED AREA IS FOUND ON 5' SIDE

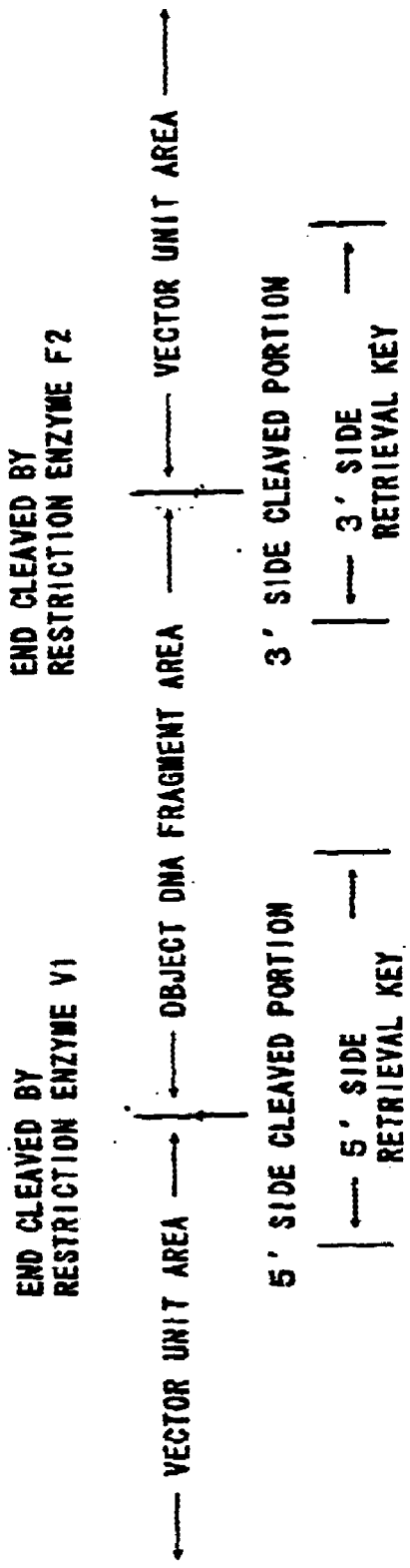
F I G. 14

WHEN HIND III IS SPECIFIED ON VECTOR 5' SIDE
XBA I IS SPECIFIED ON VECTOR 3' SIDE, HIND III IS
SPECIFIED ON OBJECT DNA 5' SIDE, AND XBA I IS
SPECIFIED ON OBJECT DNA 3' SIDE (∗∗∗∗ INDICATES RESIDUAL MULTIPLECLONING SITE
(++++ INDICATES AN OBJECT DNA FRAGMENT (SEQ ID NO. 4)                                     (SEQ ID NO. 23)
∗∗∗∗∗                      ∗∗∗∗∗∗∗∗∗∗∗∗∗∗∗∗∗∗∗∗∗∗∗∗∗∗∗∗∗∗∗∗∗∗∗∗
GTGCCAAGCTT+++++++++++++++++TCTAGAGGATCCCCGGGTACCGAGCTCGAATTCGTAAT
AAGCTT                   TCTAGA
⇧                          ⇧

5' SIDE RETRIEVAL KEY     9' SIDE RETRIEVAL KEY
(IN THIS EXAMPLE,         (IN THIS EXAMPLE, XBA I SITE)
HIND III SITE)

FIG. 17

```
┌─────────────────────────────────────────────┐  S61
│ DEFINING, IN MULTIPLE CLONING SITE OF       │
│ VECTOR, RESTRICTION ENZYME SITE USED IN     │
│ SHEARING 5' SIDE IN MULTIPLE CLONING SITE   │
│ OF VECTOR AND AREA OUTSIDE ON 5' SIDE AS    │
│ 5' SIDE RESIDUAL MULTIPLE CLONING SITE      │
│ (5MCS)                                      │
└─────────────────────────────────────────────┘
                      ⇩
┌─────────────────────────────────────────────┐  S62
│ WHEN VECTOR DB CONTAINS BASE SEQUENCE OTHER │
│ THAN MULTIPLE CLONING SITE, SUM OF 5MCS AND │
│ 5 BASES ON 5' SIDE FROM 5MCS IS DEFINED AS  │
│ 5' SIDE RESIDUAL VECTOR AREA (5VA). IF      │
│ VECTOR DB CONTAINS ONLY BASE SEQUENCE OF    │
│ MULTIPLE CLONING SITE IN VECTOR DB, THEN    │
│ 5 MCS IS 5VA.                               │
└─────────────────────────────────────────────┘
```

{ A HOMOLOGY CHECK IS MADE ACCORDING TO FOLLOWING FLOWCHART
  ON ALL ELEMENTS IN PRIMARY CANDIDATES FOR BOUNDARY PORTIONS
  (LIST 5) OBTAINED IN 5' SIDE HOMOLOGY RETRIEVAL }

```
┌─────────────────────────────────────────────┐  S63
│ DEFINING EACH CANDIDATE IN LIST 5 AND       │
│ SEQUENCE AREA OUTSIDE ON 5' SIDE AS         │
│ HOMOLOGY CHECK AREA (5HCA) FOR              │
│ CORRESPONDING CANDIDATE                     │
└─────────────────────────────────────────────┘
                      ⇩
┌─────────────────────────────────────────────┐  S64
│ COMPARING NUMBER OF BASES IN 5' SIDE        │
│ RESIDUAL VECTOR AREA (5VA), NUMBER OF       │
│ BASES OF 5HCA, AND NUMBER OF BASES 20,      │
│ AND DEFINING SMALLEST NUMBER OF BASES AS    │
│ NUMBER OF BASES FOR USE IN HOMOLOGY         │
│ CHECK (HCB)                                 │
└─────────────────────────────────────────────┘
                      ⇩
┌─────────────────────────────────────────────┐  S65
│ EXTRACTING HCB BASES FROM 3' SIDE OF 5VA    │
│ TO CHECK HOMOLOGY TO HCB BASES ON 3' SIDE   │
│ OF 5HCA                                     │
└─────────────────────────────────────────────┘
                      ⇩
┌─────────────────────────────────────────────┐  S66
│ WHEN CONSTANT HOMOLOGY IS OBTAINED,         │
│ EXTRACTED BASES ARE DEFINED AS SECONDARY    │
│ CANDIDATES FOR 5' SIDE BOUNDARY PORTIONS.   │
└─────────────────────────────────────────────┘
```

F I G. 2 0

S71: DEFINING, IN MULTIPLE CLONING SITE OF VECTOR, RESTRICTION ENZYME SITE USED IN SHEARING 3' SIDE IN MULTIPLE CLONING SITE OF VECTOR AND AREA OUTSIDE ON 3' SIDE AS 3' SIDE RESIDUAL MULTIPLE CLONING SITE (3MCS)

⇩

S72: WHEN VECTOR DB CONTAINS BASE SEQUENCE OTHER THAN MULTIPLE CLONING SITE, SUM OF 3MCS AND 5 BASES ON 3' SIDE FROM 3MCS IS DEFINED AS 3' SIDE RESIDUAL VECTOR AREA (3VA). IF VECTOR DB CONTAINS ONLY BASE SEQUENCE OF MULTIPLE CLONING SITE IN VECTOR DB, THEN 3MCS IS 3VA.

{ A HOMOLOGY CHECK IS MADE ACCORDING TO FOLLOWING FLOWCHART ON ALL ELEMENTS OF PRIMARY CANDIDATES FOR BOUNDARY PORTIONS (LIST 3) OBTAINED IN 3' SIDE HOMOLOGY RETRIEVAL }

S73: DEFINING EACH CANDIDATE IN LIST 3 AND SEQUENCE AREA OUTSIDE ON 3' SIDE AS HOMOLOGY CHECK AREA (3HCA) FOR CORRESPONDING CANDIDATE

⇩

S74: COMPARING NUMBER OF BASES IN 3' SIDE RESIDUAL VECTOR AREA (3VA), NUMBER OF BASES OF 3HCA, AND NUMBER OF BASES 20, AND DEFINING SMALLEST NUMBER OF BASES AS NUMBER OF BASES FOR USE IN HOMOLOGY CHECK (HCB)

⇩

S75: EXTRACTING HCB BASES FROM 5' SIDE OF 3VA TO CHECK HOMOLOGY TO HCB BASES ON 5' SIDE OF 3HCA

⇩

S76: WHEN CONSTANT HOMOLOGY IS OBTAINED, EXTRACTED BASES ARE DEFINED AS SECONDARY CANDIDATES FOR 3' SIDE BOUNDARY PORTIONS.

FIG. 22

```
                              SEQUENCE LISTING

<160> NUMBER OF SEQ ID NOS: 23

<210> SEQ ID NO 1
<211> LENGTH: 17
<212> TYPE: DNA
<213> ORGANISM: Homo sapiens

<400> SEQUENCE: 1
atgcatgcta gctagct                                                      17

<210> SEQ ID NO 2
<211> LENGTH: 17
<212> TYPE: DNA
<213> ORGANISM: Homo sapiens

<400> SEQUENCE: 2
tacgtacgat cgatcga                                                      17

<210> SEQ ID NO 3
<211> LENGTH: 17
<212> TYPE: DNA
<213> ORGANISM: Homo sapiens

<400> SEQUENCE: 3
agctagctag catgcat                                                      17

<210> SEQ ID NO 4
<211> LENGTH: 11
<212> TYPE: DNA
<213> ORGANISM: Homo sapiens

<400> SEQUENCE: 4
gtgccaagct t                                                            11

<210> SEQ ID NO 5
<211> LENGTH: 57
<212> TYPE: DNA
<213> ORGANISM: Homo sapiens

<400> SEQUENCE: 5
gaattcgagc tcggtacccg gggatcctct agagtcgacc tgcaggcatg caagctt          57

<210> SEQ ID NO 6
<211> LENGTH: 57
<212> TYPE: DNA
<213> ORGANISM: Homo sapiens

<400> SEQUENCE: 6
aagcttgcat gcctgcaggt cgactctaga ggatccccgg gtaccgagct cgaattc          57

<210> SEQ ID NO 7
<211> LENGTH: 18
<212> TYPE: DNA
<213> ORGANISM: Homo sapiens
```

<400> SEQUENCE: 7
tgcacttgaa cgcatgct                                                     18

<210> SEQ ID NO 8
<211> LENGTH: 17
<212> TYPE: DNA
<213> ORGANISM: Homo sapiens

<400> SEQUENCE: 8
tgcacttgaa cgctgct                                                      17

<210> SEQ ID NO 9
<211> LENGTH: 17
<212> TYPE: DNA
<213> ORGANISM: Homo sapiens

<400> SEQUENCE: 9
tgcacttgac gcatgct                                                      17

<210> SEQ ID NO 10
<211> LENGTH: 17
<212> TYPE: DNA
<213> ORGANISM: Homo sapiens

<400> SEQUENCE: 10
tgccttgaac gcatgct                                                      17

<210> SEQ ID NO 11
<211> LENGTH: 2686
<212> TYPE: DNA
<213> ORGANISM: Homo sapiens

<400> SEQUENCE: 11

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttgcatgc ctgcaggtcg | 420 |
| actctagagg atccccgggt accgagctcg aattcgtaat catggtcata gctgtttcct | 480 |
| gtgtgaaatt gttatccgct cacaattcca cacaacatac gagccggaag cataaagtgt | 540 |
| aaagcctggg gtgcctaatg agtgagctaa ctcacattaa ttgcgttgcg ctcactgccc | 600 |
| gctttccagt cgggaaacct gtcgtgccag ctgcattaat gaatcggcca acgcgcgggg | 660 |
| agaggcggtt tgcgtattgg gcgctcttcc gcttcctcgc tcactgactc gctgcgctcg | 720 |
| gtcgttcggc tgcggcgagc ggtatcagct cactcaaagg cggtaatacg gttatccaca | 780 |
| gaatcagggg ataacgcagg aaagaacatg tgagcaaaag gccagcaaaa ggccaggaac | 840 |
| cgtaaaaagg ccgcgttgct ggcgtttttc cataggctcc gcccccctga cgagcatcac | 900 |
| aaaaatcgac gctcaagtca gaggtggcga aacccgacag gactataaag ataccaggcg | 960 |
| tttccccctg gaagctccct cgtgcgctct cctgttccga cctgccgct taccggatac | 1020 |
| ctgtccgcct ttctcccttc gggaagcgtg gcgctttcct aaagctcacg ctgtaggtat | 1080 |

```
ctcagttcgg tgtaggtcgt tcgctccaag ctgggctgtg tgcacgaacc ccccgttcag        1140
cccgaccgct gcgccttatc cggtaactat cgtcttgagt ccaacccggt aagacacgac        1200
ttatcgccac tggcagcagc cactggtaac aggattagca gagcgaggta tgtaggcggt        1260
gctacagagt tcttgaagtg gtggcctaac tacggctaca ctagaagaac agtatttggt        1320
atctgcgctc tgctgaagcc agttaccttc ggaaaaagag ttggtagctc ttgatccggc        1380
aaacaaacca ccgctggtag cggtggtttt tttgtttgca agcagcagat tacgcgcaga        1440 aaaaaggat ctcaagaaga cctttgatc ttttctacgg ggtctgacgc tcagtggaac         1500
gaaaactcac gttaagggat tttggtcatg agattatcaa aaggatcttc acctagatc         1560 cttttaaatt aaaatgaag ttttaaatca atctaaagta tatatgagta aacttggtct        1620
gacagttacc aatgcttaat cagtgaggca cctatctcag cgatctgtct atttcgttca        1680
tccatagttg cctgactccc cgtcgtgtag ataactacga tacgggaggg cttaccatct        1740
ggccccagtg ctgcaatgat accgcgagac ccacgctcac cggctccaga tttatcagca        1800 ataaccagc cagccggaag ggccgagcgc agaagtggtc ctgcaacttt atccgcctcc         1860
atccagtcta ttaattgttg ccgggaagct agagtaagta gttcgccagt taatagtttg        1920
cgcaacgttg ttgccattgc tacaggcatc gtggtgtcac gctcgtcgtt tggtatggct        1980
tcattcagct ccggttccca acgatcaagg cgagttacat gatcccccat gttgtgcaaa        2040
aaagcggtta gctccttcgg tcctccgatc gttgtcagaa gtaagttggc cgcagtgtta        2100
tcactcatgg ttatggcagc actgcataat tctcttactg tcatgccatc cgtaagatgc        2160
ttttctgtga ctggtgagta ctcaaccaag tcattctgag aatagtgtat gcggcgaccg        2220
agttgctctt gcccggcgtc aatacgggat aataccgcgc cacatagcag aactttaaaa        2280
gtgctcatca ttggaaaacg ttcttcgggg cgaaaactct caaggatctt accgctgttg        2340
agatccagtt cgatgtaacc cactcgtgca cccaactgat cttcagcatc ttttactttc        2400
accagcgttt ctgggtgagc aaaaacagga aggcaaaatg ccgcaaaaaa gggaataagg        2460
gcgacacgga aatgttgaat actcatactc ttccttttc aatattattg aagcatttat         2520
cagggttatt gtctcatgag cggatacata tttgaatgta tttagaaaaa taaacaaata        2580
ggggttccgc gcacatttcc ccgaaaagtg ccacctgacg tctaagaaac cattattatc        2640
atgacattaa cctataaaaa taggcgtatc acgaggccct ttcgtc                      2686
```

<210> SEQ ID NO 12
<211> LENGTH: 67
<212> TYPE: DNA
<213> ORGANISM: Homo sapiens

<400> SEQUENCE: 12

```
gtgccaagct tgcatgcctg caggtcgact ctagaggatc cccgggtacc gagctcgaat         60
tcgtaat                                                                   67
```

<210> SEQ ID NO 13
<211> LENGTH: 6
<212> TYPE: DNA
<213> ORGANISM: Homo sapiens

<400> SEQUENCE: 13

```
aagctt                                                                     6
```

<210> SEQ ID NO 14
<211> LENGTH: 6

-continued

```
<212> TYPE: DNA
<213> ORGANISM: Homo sapiens

<400> SEQUENCE: 14 gcatgc                                                                        6

<210> SEQ ID NO 15
<211> LENGTH: 6
<212> TYPE: DNA
<213> ORGANISM: Homo sapiens

<400> SEQUENCE: 15 ctgcag                                                                        6

<210> SEQ ID NO 16
<211> LENGTH: 6
<212> TYPE: DNA
<213> ORGANISM: Homo sapiens

<400> SEQUENCE: 16 gtcgac                                                                        6

<210> SEQ ID NO 17
<211> LENGTH: 6
<212> TYPE: DNA
<213> ORGANISM: Homo sapiens

<400> SEQUENCE: 17 tctaga                                                                        6

<210> SEQ ID NO 18
<211> LENGTH: 6
<212> TYPE: DNA
<213> ORGANISM: Homo sapiens

<400> SEQUENCE: 18 ggatcc                                                                        6

<210> SEQ ID NO 19
<211> LENGTH: 6
<212> TYPE: DNA
<213> ORGANISM: Homo sapiens

<400> SEQUENCE: 19 cccggg                                                                        6

<210> SEQ ID NO 20
<211> LENGTH: 6
<212> TYPE: DNA
<213> ORGANISM: Homo sapiens

<400> SEQUENCE: 20 ggtacc                                                                        6

<210> SEQ ID NO 21
<211> LENGTH: 6
<212> TYPE: DNA
<213> ORGANISM: Homo sapiens

<400> SEQUENCE: 21 gagctc                                                                        6

<210> SEQ ID NO 22
```

-continued

```
<211> LENGTH: 6
<212> TYPE: DNA
<213> ORGANISM: Homo sapiens

<400> SEQUENCE: 22 gaattc                                                                  6

<210> SEQ ID NO 23
<211> LENGTH: 38
<212> TYPE: DNA
<213> ORGANISM: Homo sapiens

<400> SEQUENCE: 23
tctagaggat ccccgggtac cgagctcgaa ttcgtaat                              38
```

METHOD AND APPARATUS FOR AUTOMATICALLY REMOVING VECTOR UNIT IN DNA BASE SEQUENCE

This application is a Continuation of application Ser. No. 08/684,674, filed Jul. 22, 1996, now abandoned.

BACKGROUND OF THE INVENTION

1. Field of the Invention

The present invention relates to an automatic vector unit removing method for automatically removing a part of the vector inside a fragment of an object DNA when it is taken out of a proliferated vector in a DNA cloning. The DNA cloning process is performed to proliferate a fragment of the object DNA by chemically bonding a clone, that is, a fragment of a DNA containing a gene to be proliferated to a DNA molecule called a vector, and then proliferating the vector in cells such as *Escherichia coli*, etc.

2. Description of the Related Art

A nucleic acid is formed by nucleotide composed of a base, pentose, and phosphoric acid. The nucleotide is a compound of a nucleoside and a phosphoric acid. The phosphoric acid forms a polymer through the nucleoside to produce either a deoxyribonucleic acid (DNA) or ribonucleic acid (RNA).

The bases forming part of the nucleic acid can be a purine or a pyrimidine. The purine can be an adenine A or a guanine G while the pyrimidine can be a cytosine C or a thymine T.

The DNA having the composition called a polynucleotide strand is formed by a strand of the above listed four bases, that is, the adenine A, guanine G. cytosine C, and thymine T, bound in a series. For example, if a DNA is extracted from the chromosome in the cell of a human being and is arranged as a sequence, it can be as long as 1 meter and contain 3 billion bases.

Thus, a DNA has a strand of bases, that is, a base sequence linked in the form of a strand. The strand is normally very long. In genetic engineering, a DNA including venous genes is cleaved for gene recombination, and a DNA fragment having specific genetic information is extracted from a number of the cleaved DNA fragments. The extracted DNA fragments, that is, object DNA fragments, should be normally proliferated.

Normally, a unique sequence of object DNA fragments is very small in volume, and the object DNA fragments are combined with a vector to perform the cloning for DNA sequencing.

To attain this, the object DNA fragments are chemically bound to the DNA called a vector which is normally a circular DNA. The combination of the object DNA fragment and the vector DNA, that is, a recombinant DNA, is integrated into an appropriate cell such as a colibacilli (colon bacillus), and the cell is proliferated to produce a large volume of the recombinant DNA. As a result, the cloning process of generating a large volume of the object DNA fragments is successfully performed.

A vector is commonly a DNA having a double helix structure a specific portion of which is cleaved using some restriction enzymes. The object DNA fragment is integrated into the cleaved portion. Before describing the cleaving of the DNA using the restriction enzyme, the structure of the DNA is explained below.

A DNA has the structure of a base sequence, that is, a sequence of bases bound in the form of a strand. Since the DNA strand is directional, ATGCACGA→ is different from ATGCACGA← (which equals AGCACGTA→).

Both ends of the DNA strand are named. Accordingly, the end provided with a hydroxyl group at the position of 3' of a saccharum is called a 3' end. The other end, that is, the end provided with a phosphate group at the position of 5' of a saccharum is called a 5' end. When the DNA strand is described, the 5' end is positioned on the left while the 3' end is positioned on the right.

A DNA normally exists in a double-stranded state as two complementary and anisotropic base sequences. In the two base sequences, the facing bases have a fixed relationship, and the adenine A faces the thymine T, while the guanine G faces the cytosine C. An example of a DNA double-strand is shown as follows:

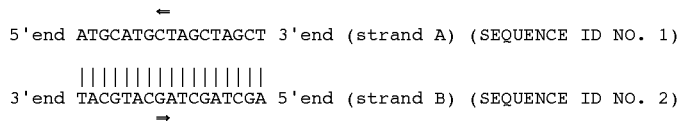

5'end ATGCATGCTAGCTAGCT 3'end (strand A) (SEQUENCE ID NO. 1)
3'end TACGTACGATCGATCGA 5'end (strand B) (SEQUENCE ID NO. 2)

Strand B is complementary to strand A and is represented as a single strand as follows:

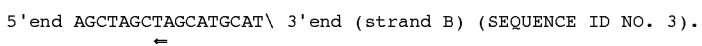

5'end AGCTAGCTAGCATGCAT\ 3'end (strand B) (SEQUENCE ID NO. 3).

Thus, the DNA represents a genetic meaning with the two complementary base sequences as a pair. The base sequences unique to the restriction enzyme are identified to shear the DNA at the identified points.

FIG. 1 shows how the DNA base sequence is cleaved using the restriction enzyme. In FIG. 1, the restriction enzyme called HpaI shears the DNA at the same positions on the two strands of the DNA whereas the restriction enzymes EcoRI and Hind III shear double strands at different points on the two strands.

As shown in FIG. 1, a number of restriction enzymes can identify nucleotide sequences formed by 6 pairs of bases. The two nucleotide strands in the identification area, that is, the site of the restriction enzyme, are arranged in the opposite directions. Most restriction enzymes indicate different cleaving positions on two strands, thereby forming uneven ends, that is, cohesive ends. The above described object DNA fragments are integrated into the positions where the DNA is cleaved based on the restriction enzymes.

FIG. 2 shows how to mount the object DNA fragments in the vector. In FIG. 2, the circular plasmid DNA molecule is cleaved by the restriction enzymes to obtain linear plasmid DNA molecules having cohesive ends. A plasmid is contained in, for example, bacteria, and can autonomously proliferate unlike the chromosome DNA. The linear plasmid DNA molecule and the object DNA fragments, that is, one of various DNA fragments obtained by cleaving the chromosome DNA using the restriction enzymes, form base pairs. This is referred to as annealing at cohesive ends, thereby forming a circular DNA.

Thus, the cohesive ends generated by the restriction enzymes are required for the recombinant DNA technology. Actually, any DNA fragments can be bound to a plasmid DNA by cleaving the DNA using the restriction enzymes used in generating the object DNA fragments. The linear plasmid DNA molecule is bound to the object DNA fragments through the DNA ligase for repair of the cleaved portion in a single strand of the double stranded DNA, thereby generating a chromosome-DNA-integrated plasmid DNA molecule.

The generated plasmid DNA molecule can be proliferated in bacteria or enzymes. The process is called a DNA cloning technology.

FIG. 3 shows the vector used in the DNA cloning process and the multiple cloning site in the vector. A number of restriction enzyme sites to be cleaved by various restriction enzymes is concentrated in the multiple cloning site.

When an object DNA fragment is taken out of a large amount of the plasmid DNA molecules generated as a result of the DNA cloning process, the nucleotide sequence of the DNA fragment processed in the cloning operation should be correctly determined and the bases in unnecessary portions are deleted to take out a DNA fragment having a correct structure. To determine the nucleotide sequence in the DNA fragment, a DNA sequencer is used to automatically read the DNA base sequence.

To know the sequence of A, G, T, and C in the DNA is to understand the genetic information. The sequence technology for determining the base sequence has advanced with the technologies of other fields, and is closely related to the discovery of the restriction enzymes and nucleic acids, and the development in technology for DNA cloning, nucleic acid chemistry, etc.

Recently, computer technology has been utilized as one of the sequence methods, thereby enabling an enormous volume of data to be input end accumulated. Thus, computers are required in determining the base sequence.

With the DNA sequencer for automatically reading the base sequence of the DNA, the dideoxy method or the Sanger method is used to determine a base sequence. Normally when a part of one of the two complementary DNA strands is used as a primer, which can be a trigger in synthesizing a DNA, the DNA synthesis is stopped when a dideoxynucleotide is integrated, and the DNA fragments with variations in length can be obtained. If the dideoxynucleotide is applied corresponding to each base of G, A, T, and C in the DNA synthetic reaction using a primer, then the DNA fragments with variations in length can be obtained with the growth of strands stopped at the position of each base.

FIG. 4 shows a specific nucleotide, and how to obtain the DNA fragments by cleaving the DNA at the adenine A. In this case, a moderate chemical process of removing a piece of nucleotide, that is, the adenine A, from a DNA strand is performed. Only the left fragments provided with a phosphate group at the 5' end are radioactive. If these fragments are processed in a gel electrophoresis, the radioactive fragments are detected by the length of the fragment, that is, at the position corresponding to the molecular weight.

With the DNA sequencer, the DNA fragment is fluorescent-identified as a reactive product in the dideoxy method. As a result, the fluorescent-identified DNA fragments having strands with variations in length are separated through the gel electrophoresis. A fluorescent color element is excited and luminous at a point on the gel by irradiation of a laser light on the DNA fragment in the gel electrophoresis. The fluorescent light is detected by a light detector. By detecting the fluorescent light with the time of the electrophoresis, the data of the electrophoresis pattern of the DNA fragments corresponding to each base of the G, A, T, and C can be obtained. The obtained data is analyzed by the computer and converted into base sequence data.

Usually, the output data of the DNA sequencer includes a DNA base sequence itself and the waveform data used in determining the sequence. The waveform data corresponds to the data of the gel electrophoresis pattern. In each waveform of the G, A, T, and C, the position of the peak of the fluorescence intensity of the waveform corresponds to the position of the base.

However, the number of bases in the DNA base sequence is normally large as described above. Therefore, the DNA sequencer cannot simultaneously determine all base sequences. Therefore, an object DNA whose sequence is to be determined is divided into a plurality of fragments. Then, the base sequence of each fragment is determined and they are bound to each other, thereby determining the entire base sequence.

When an object DNA fragment is generated by the above described method, the sequence result as an output of the sequencer contains a part of the base sequence of the vector used in the cloning process in addition to the object DNA fragment. The prior art technology has the problem that it is very important to delete the part of the base.

The vector unit is a part of the bases in the vector, and it is probably contained in the 5' end portion and 3' end portion obtained as sequence results. To generate a correct object DNA fragment, the vector unit should be completely removed. Conventionally, the vector unit has been removed through a homology search, which is a retrieval method for outputting a retrieval result using the base sequence of the vector unit possibly positioned before or after the object DNA fragment base sequence, even if all bases do not completely match. However, this method has the problem that the vector unit cannot be successfully detected because the base sequence of the vector unit may be short, or a mis-sequencing operation, etc. at the 3' end badly affects the vector-unit detection.

SUMMARY OF THE INVENTION

The present invention aims at providing a method and device for retrieving the vector unit mixed in the DNA sequence result and automatically deleting the vector unit from the retrieval result.

A vector unit base sequence removing method according to the invention is used for removing a vector unit base sequence from a DNA base sequence which is obtained as a result of performing a cloning process by integrating an object DNA fragment into a vector, and includes the vector unit base sequence as a part of a base sequence of the vector and the object DNA fragment. The method includes the steps of: generating a retrieval base sequence as a retrieval key for use in retrieving the vector unit base sequence from the DNA base sequence based on the vector, a restriction enzyme used to cleave the vector for cloning the cloning process, and a restriction enzyme used to obtain the object DNA fragment; specifying the vector unit base sequence using the retrieval key; and removing the specified vector unit base sequence to specify the object DNA fragment.

The DNA base sequence may be obtained as an output from a sequencer for determining the DNA base sequence.

The retrieval key may include a forward (leading) retrieval key and a backward (following) retrieval key for respectively identifying areas before and after the object DNA fragment in the DNA base sequence. The forward and backward retrieval keys may indicate the base sequences corresponding to restriction enzyme sites including parts of the vector cleaved by a restriction enzyme for the cloning process and ends of the object DNA fragment.

Base sequences of the forward and backward retrieval keys may be generated by base sequence data of the vector entered in a vector data base, data of a multiple cloning site in the vector, and data of a restriction enzyme site in the multiple cloning site.

The method according to the present invention may further include the steps of: performing homology retrieval on condition that a similarity value indicating a matching rate between the retrieval base sequence and the DNA base sequence is equal to or larger than a predetermined value in retrieval using the retrieval key for the DNA base sequence; and obtaining a candidate for a base sequence at a junction between the vector in the DNA base sequence and the object DNA fragment according to a result of the homology retrieval.

The method according to the present invention may further include the steps of: generating a second forward retrieval key by adding to the forward retrieval key a portion that should be existing before the multiple cloning site of the vector; performing a second homology retrieval on condition that a second similarity value indicating a matching rate between a base sequence corresponding to the second forward retrieval key and a base sequence including a base sequence at a junction of the DNA base sequence is equal to or larger then a predetermined value; end obtaining as a vector unit candidate for the vector unit base sequence an area specified as a result of the second homology retrieval and an area or areas before the specified area.

The method according to the present invention may further include the stops of: generating a second backward retrieval key by adding to the backward retrieval key a portion that should be existing after the multiple cloning site of the vector; performing a second homology retrieval on condition that a second similarity value indicating a matching rate between a base sequence corresponding to the second backward retrieval key and a base sequence containing the base sequence at the junction of the DNA base sequence is equal to or larger than a predetermined value; end obtaining as a vector unit candidate for the vector unit base sequence an area specified as a result of the second homology retrieval and an area or areas after the specified area.

The vector unit candidate may be removed from the DNA base sequence when the number of the area specified by the second homology retrieval is one.

The method according to the present invention may further include the steps of: generating a second forward retrieval key by adding to the forward retrieval key a portion that should be existing before the multiple cloning site of the vector; generating a second backward retrieval key by adding to the backward retrieval key a portion that should be existing after the multiple cloning site of the vector; performing a second homology retrieval on condition that a second similarity value indicating a matching rate between a base sequence corresponding to the second forward retrieval key and a base sequence including a base sequence at a junction of the DNA base sequence is equal to or larger than a predetermined value, and a third similarity value indicating a matching rate between a base sequence corresponding to the second backward retrieval key and a base sequence including the base sequence, at a junction of the DNA base sequence is equal to or larger than a predetermined value; obtaining as a forward vector unit candidate for the vector unit base sequence a forward area specified as a result of the second homology retrieval and an area before the forward area; and obtaining as a backward vector unit candidate for the vector unit base sequence a backward area specified as a result of the second homology retrieval and an area after the backward area.

The forward vector unit candidate and the backward vector unit candidate may be removed from the DNA base sequence when there is only one candidate respectively for the specified forward and backward vector units, and the specified forward and backward vector units do not overlap each other.

A vector unit base sequence removing device according to the invention is for removing a vector unit base sequence from a DNA base sequence which is obtained as a result of performing a cloning process by integrating an object DNA fragment into a vector and includes the vector unit base sequence as a part of a base sequence of the vector end the object DNA fragment. The device includes: a first unit for generating a base sequence as a retrieval key for use in retrieving the vector unit base sequence from the DNA base sequence based on the vector, a first restriction enzyme used to cleave the vector for the cloning process, and a second restriction enzyme used to obtain the object DNA fragment; a second unit for specifying the vector unit base sequence using the retrieval key; and a third unit for removing the specified vector unit base sequence to specify the object DNA fragment.

The device according to the present invention may further include: a vector list storage unit for storing a vector list; and a restriction enzyme list storage unit for storing a restriction enzyme list. The vector is specified in the vector list, and the first and second restriction enzymes are specified in the restriction enzyme list.

The device according to the present invention may further include a display unit. The vector may be specified in the vector list displayed on the display unit, and at least one of the first and second restriction enzymes may be specified in the restriction enzyme list displayed on the display unit.

The device according to the present invention may further include a program storage unit for storing at least one of: a program for generating the retrieval key by controlling the first unit; a program for specifying the vector unit base sequence by controlling the second unit; and a program for removing the vector unit base sequence by controlling the third unit.

The second unit may specify, using the retrieval key, a junction between the vector unit base sequence and the object DNA fragment, and the third unit may specify the object DNA fragment by removing the junction and a portion outside the junction from the DNA base sequence.

The second unit may specify as the junction a portion in the DNA sequence in which a number of bases matching a base sequence of the retrieval key is equal to or larger than a predetermined value.

The second unit may specify using the retrieval key a first junction and a second junction between the vector unit base sequence and the object DNA fragment, and the third unit may specify the object DNA fragment by removing from the DNA base sequence the first junction and a portion outside the first junction and the second junction and a portion outside the second junction.

The retrieval key may include a base sequence corresponding to an end portion of the object DNA fragment and a base sequence corresponding to an end portion of the vector unit base sequence, and may specify a candidate for a junction between the vector unit base sequence and the object DNA fragment.

A second retrieval key indicating a base sequence longer than the retrieval key may be generated, and the junction may be specified among the candidates for the junction using the second retrieval key.

The object DNA fragment may be specified by removing the junction and a portion outside the junction from the DNA base sequence.

A storage medium according to the invention is for embodying a program for performing, by a computer, a function of removing a vector unit base sequence from a DNA base sequence which is obtained as a result of performing a cloning process by integrating an object DNA fragment into a vector and includes the vector unit base sequence as a part of a base sequence of the vector and the object DNA fragment. The program realizes the steps of: generating a retrieval base sequence as a retrieval key for use in retrieving the vector unit base sequence from the DNA base sequence based on the vector, a restriction enzyme used to cleave the vector for the cloning process, and a restriction enzyme used to obtain the object DNA fragment; specifying the vector unit base sequence using the retrieval key; and removing the specified vector unit base sequence to specify the object DNA fragment.

The above described methods and the methods explained in the following embodiment may be realized using computer programs. The methods according to the present invention may be realized using storage media such as diskettes, CDROM, hard disks, mini-disks, RAM, etc.

BRIEF DESCRIPTION OF THE DRAWINGS

FIG. 5 is a block diagram showing a vector removing method of the present invention;

FIG. 8 shows an example of a vector list stored in the vector data base;

FIG. 9 shows the base sequence of the vector PUC18;

FIG. 10 shows the multiple cloning site of the vector PUC18 and the restriction enzyme information;

FIG. 11 shows the restriction enzyme list for the vector PUC18;

FIG. 12 is a flowchart showing the entire process performed by the vector unit specification program;

FIGS. 13A, 13B, and 13C show the restriction enzyme site;

FIG. 14 shows the object DNA fragment integrated into a vector;

FIG. 17 shows the retrieval key for homology retrieving for use in the vector unit specification program;

FIG. 20 is a flowchart showing the process of retrieving a secondary candidate for the 5' side boundary portion;

FIG. 22 is a flowchart showing the process of retrieving a secondary candidate for the 3' side boundary portion;

DESCRIPTION OF THE PREFERRED EMBODIMENT

Figure 1:
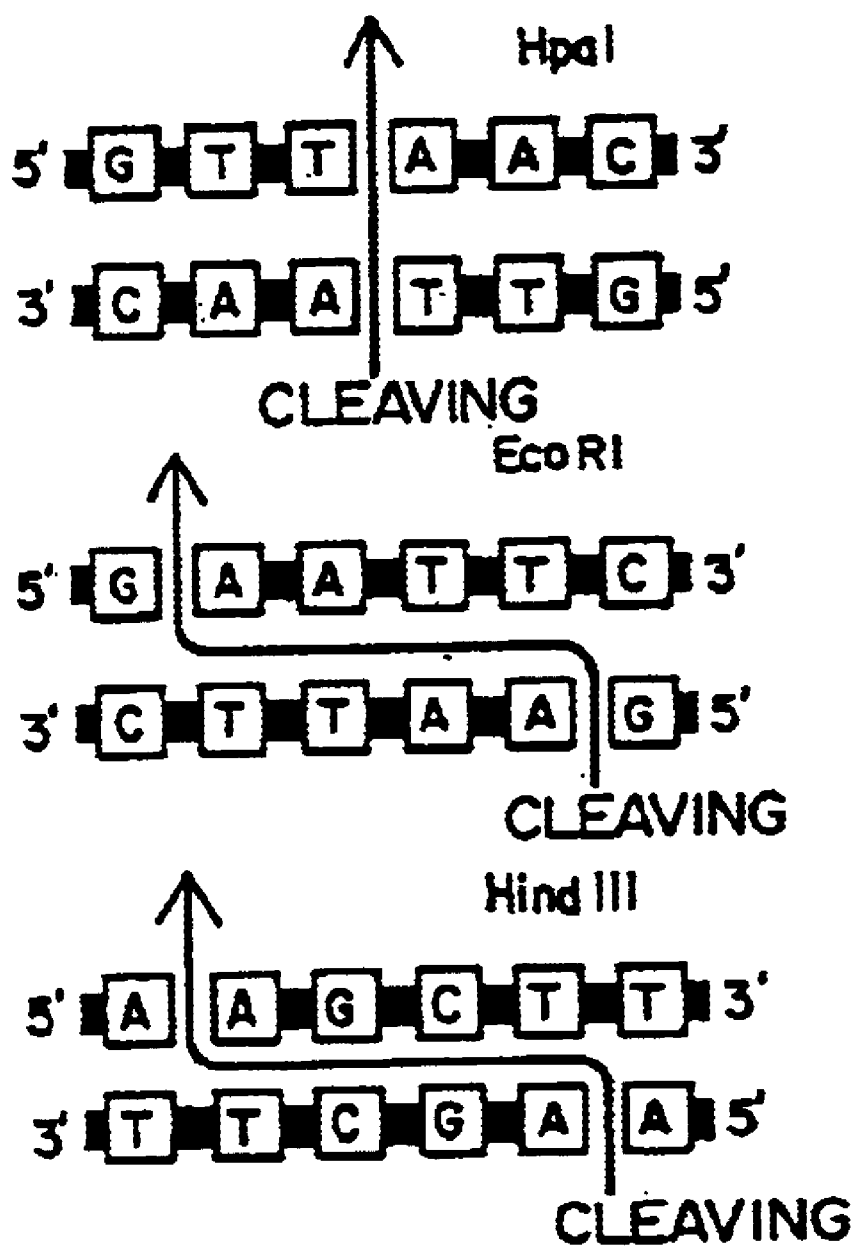
FIG. 1 shows an example of cleaving DNA base sequences using restriction enzymes.

FIG. 5 is a block diagram showing the functions of an automatic vector unit removing method of the automatic vector unit removing method of the present invention. In general, the vector, for example, a circular plasmid DNA molecule, is cleaved, and en object DNA fragment is integrated into the cleaved portion in a cloning-process. The automatic vector unit removing method according to the present invention removes the base sequence of a portion of the vector unit contained in the object DNA fragment from the object DNA fragment retrieved from the vectors generated through the DNA cloning process.

In step 1 shown in FIG. 5, a base sequence is generated as a retrieval key for use in retrieving the vector unit base sequence from the DNA base sequence obtained as a result of the cloning process. It is generated according to the type of vector, the restriction enzyme used in integrating the object DNA fragment, and the restriction enzyme used in obtaining the object DNA base sequence. In step 2, the vector unit base sequence is specified using the generated retrieval key, and the specified vector unit base sequence is automatically removed.

For example, a forward retrieval key and a backward retrieval key are used as the above described retrieval keys. These retrieval keys contain the ends cleaved by the restriction enzymes corresponding to the vector unit and object DNA fragment in the DNA fragment in the DNA base sequence obtained as a cloning result. The keys contain the base sequence corresponding to the restriction enzyme site before the chemical bonding of the vector unit and the object DNA fragments respectively. The forward retrieval key is positioned before the object DNA fragment while the backward retrieval key is positioned after the object DNA fragment.

In the retrieval performed using the forward and backward retrieval keys in the DNA base sequence obtained as a result of the cloning process, the homology retrieval is performed on condition that a value larger than a predetermined similarity can be obtained. The retrieval result is obtained as a candidate for a conjugative unit between the vector and the object DNA fragment. Of the candidates for a conjugative unit between the vector and the object DNA fragment, the primary candidate at the 5' boundary point corresponds to the forward retrieval key while the primary candidate at the 3' boundary point corresponds to the backward retrieval key.

Since there can be a plurality of the primary candidates respectively at the 3' and 5' boundary points, the retrieval processes are further performed using the second forward and backward retrieval keys according to the present invention. The second forward and backward retrieval keys are the same as the above described forward or backward retrieval keys, in the multiple cloning site of a vector, provided with the adjacent portions before or after the key. The homology retrieval is performed on these forward and backward retrieval keys. In consideration of the retrieval result, all areas before or after the retrieval result are specified as a candidate for the vector unit.

If a single candidate for a vector unit is detected before and after the object DNA fragment respectively, and if the forward vector unit candidate does not overlap the backward vector unit candidate, then the specified vector unit candidates are automatically removed as vector units.

Thus, according to the present invention, the primary candidates at the boundary portions are obtained using, for example, the base sequence of the restriction enzyme site as the forward retrieval key and backward retrieval key. Then, a candidate for a vector unit is obtained by the homology retrieval based on the second forward and backward retrieval keys including the primary candidates and portions of the base sequences before and after the forward and backward retrieval keys, respectively. Thus, the vector unit can be automatically removed when an approximate candidate has been obtained for the vector unit.

Figure 6:
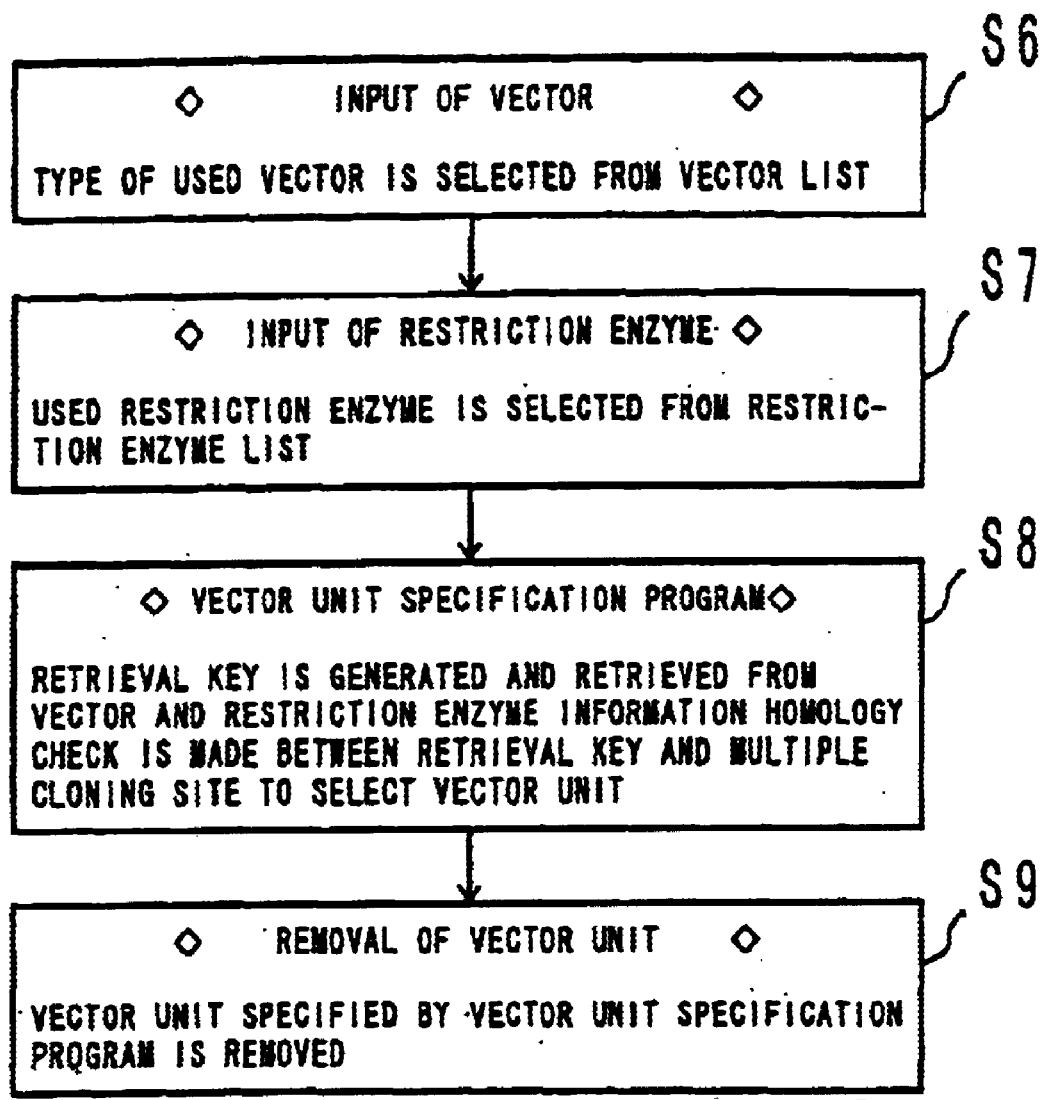
FIG. 6 is a flowchart of the basic process of the automatic vector unit removing method.

FIG. 6 is a flowchart showing the basic process of the automatic vector unit removing method according to the present invention. As shown in FIG. 6, the method includes steps S6 through S9. Instep S8, the type of the vector used in the cloning process is selected from the vector list and entered. In step S7, the restriction enzyme used in the cloning process is selected from the restriction enzyme list and entered, in step S8, a retrieval key is generated based on the information about the vector and restriction enzyme, and the vector unit is retrieved according to the retrieval key. That is, the homology between the retrieval key and the multiple cloning site is checked, and the vector unit specification program is executed to select the vector unit. In step S9, the vector unit specified by the vector unit specification program is removed, thus terminating the process.

Figure 7:
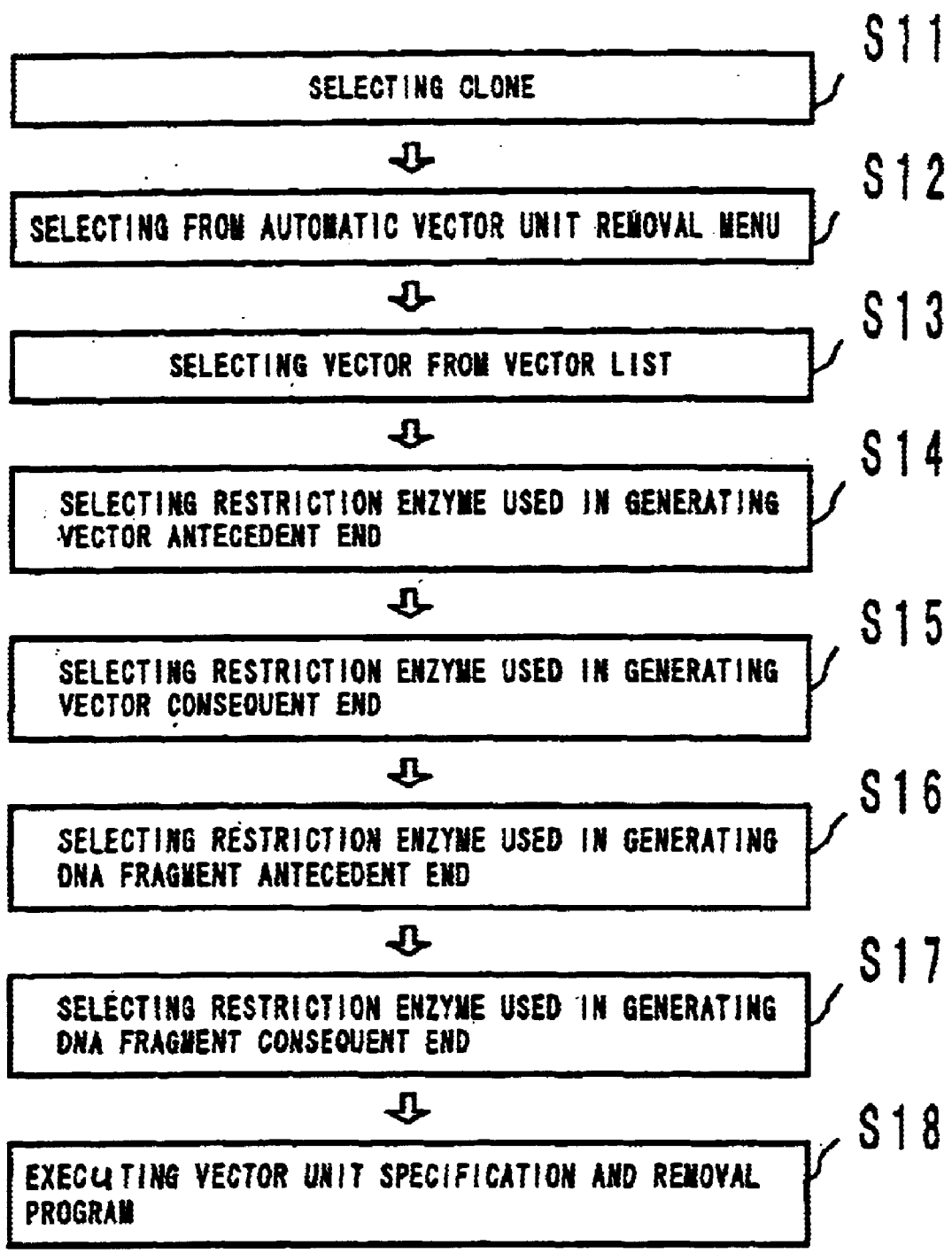
FIG. 7 is a flowchart showing the automatic vector unit removing process according to the present invention.

FIG. 7 is a flowchart showing the automatic vector unit removing process (corresponding to steps S8 and S9 shown in FIG. 6) according to the present invention. In the automatic vector unit removing process, a vector unit is automatically removed from a DNA base sequence read using a DNA sequencer (fragment).

As shown in FIG. 7, the process includes steps S11 to S18. A clone (DNA fragment) to be processed in the automatic vector unit is selected in step S11. In step S12, the automatic vector unit removing process is specified by the user from the menu displayed on the display unit. Thus, the automatic vector unit removing dialog (interactive menu) is displayed. In step S13, the used vector is selected from the vector list through the dialog.

Using the automatic vector unit removing dialog, the restriction enzymes used in generating the cleaved portions at the front and back of the vectors and the object DNA are selected in steps S14 through S17. Normally, four types of restriction enzymes are selected, but the selected restriction enzymes are not limited to four types. In step S18, a vector unit specification and removal program is executed to remove the vector unit based on the selected restriction enzymes, thus terminating the process.

Before describing in detail the vector unit specification and removal program, the processes in other steps will be described.

First, in step S11, a clone whose vector is to be automatically deleted is selected from the clones displayed in the main window on the display unit. When the user selects the vector unit specification and removal menu from the menu items displayed on the display unit in step S12, the vector/restriction enzyme selection dialog is opened. The vector names entered in the vector data base are listed in the dialog, and an actually used vector is selected from the vector list in step S13.

FIG. 8 shows an example of a vector name list entered in the vector data base. PUC 18 is selected from the list shown in FIG. 8 according to the present embodiment.

If a vector is selected, the data of the base sequences in the multiple cloning site of the selected vector and the data of the restriction enzyme site are extracted, and the name of the restriction enzyme corresponding to the restriction enzyme site in the multiple cloning site is displayed.

FIG. 9 shows the base sequence of PUC 18 stored in the vector data base. In FIG. 9, the multiple cloning site is indicated as underlined (starts from A, the second from the end of line 5, and ends at C, the 26th from the end of line 6).

In step S13, the multiple cloning site and the base sequence containing 5 bases before and after the multiple cloning site are extracted from the data base for the vector (PUC 18 in this example) selected in step S13 in order to hold the largest possible number of character strings of retrieval keys for efficient retrieval. The restriction enzyme information, that is, the names of restriction enzymes, base sequences, positions of the restriction enzyme sites, and the cleaving point data, are extracted from the data base corresponding to the restriction enzyme site in the multiple cloning site. FIG. 10 shows an example of the thus extracted multiple cloning site and the restriction enzyme information.

After the used vector is selected and the multiple cloning site and the restriction enzyme information are extracted in step S13 in FIG. 7, in steps S14 through S17, four restriction enzymes used in cleaving the DNA strands at the 5' and 3' are selected according to extracted information. The selection is made by specifying used restriction enzymes from the restriction enzyme list shown in FIG. 11. FIG. 11 shows a last of the restriction enzymes used when PUC 18 is selected as a vector. The restriction enzyme list stores the restriction enzymes for use in cleaving the restriction enzyme site in the multiple cloning site of the vectors.

Figure 2:
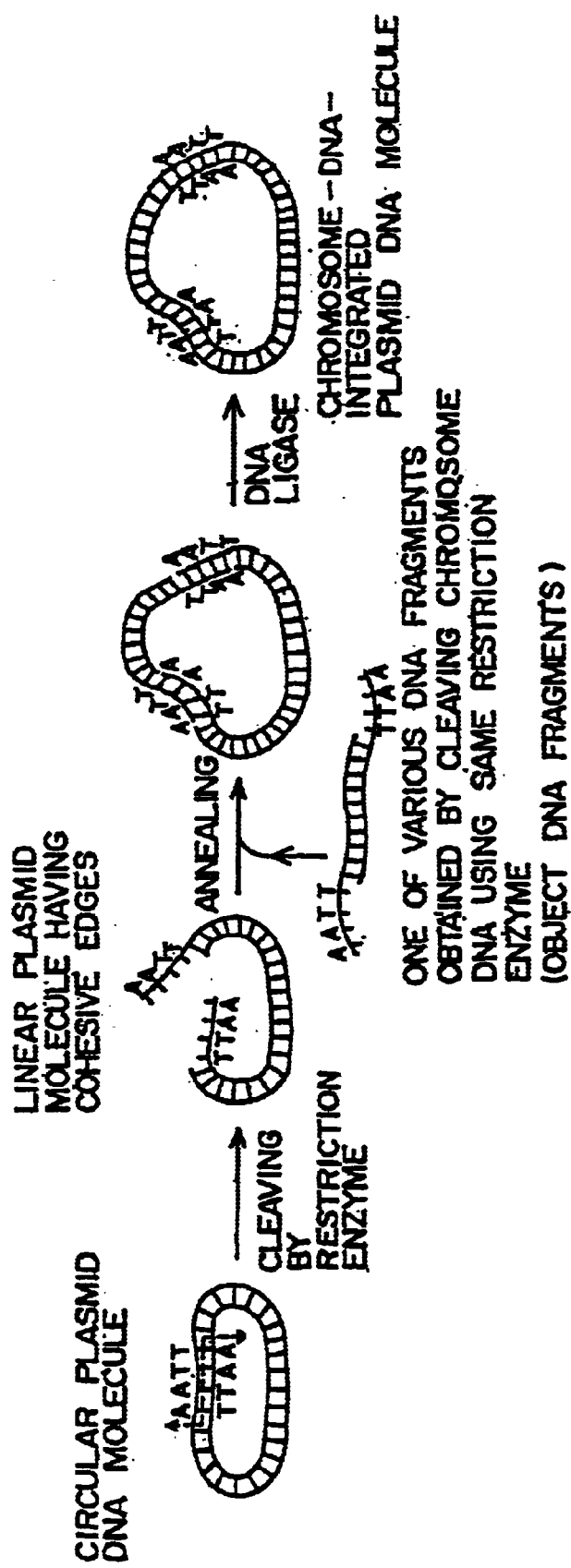
FIG. 2 shows the operation of binding an object DNA fragment into a circular plasmid DNA molecule.
Figure 3:
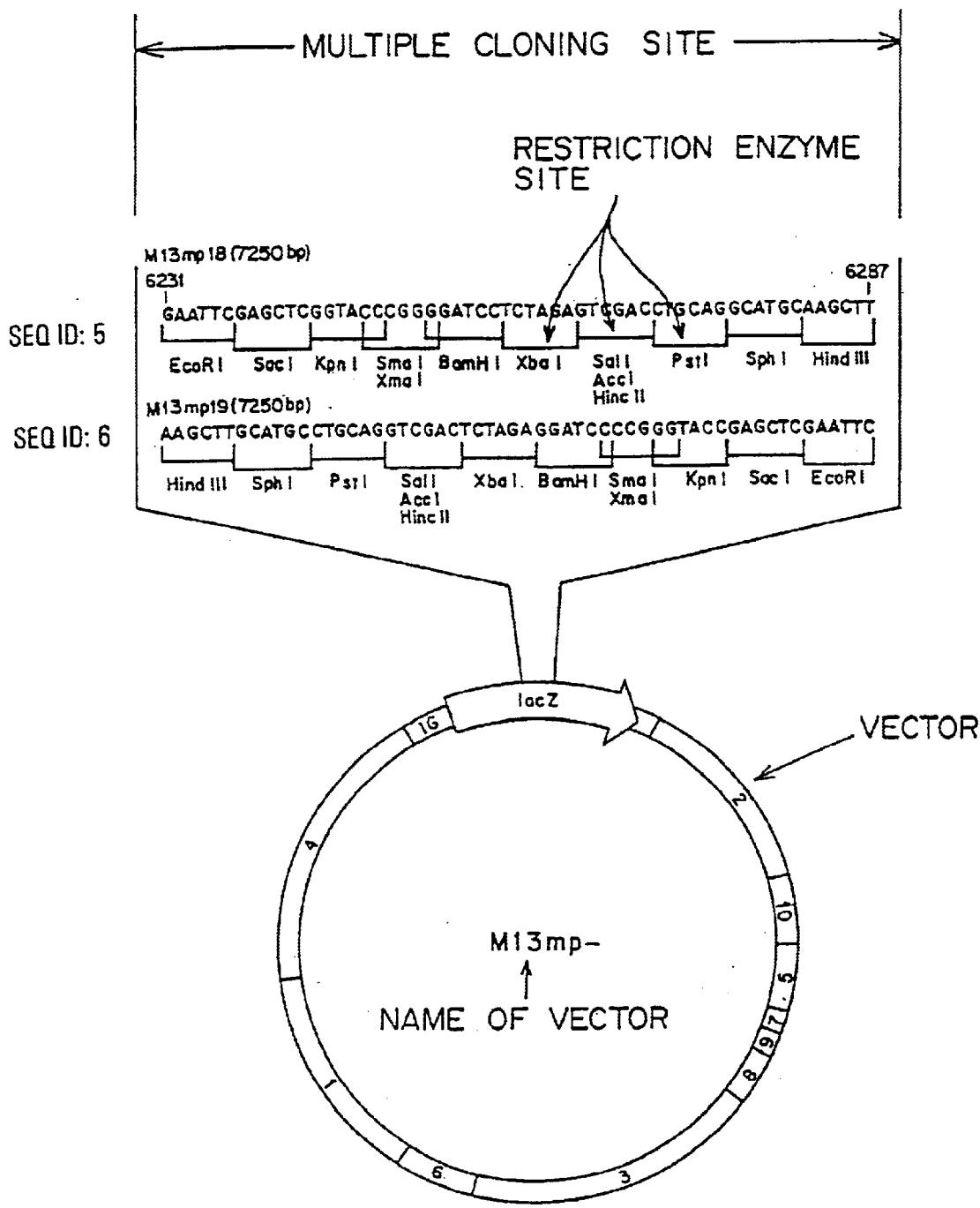
FIG. 3 shows an example of a vector and multiple cloning site.
Figure 4:
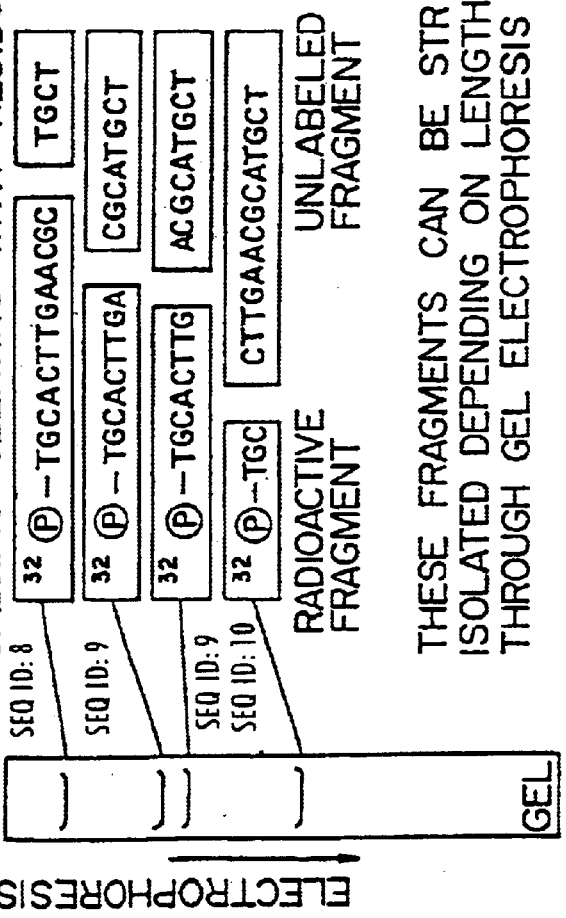
FIG. 4 shows how to generate a DNA fragment.

If four restriction enzymes are selected in steps S14 through S17, then a retrieval key for use in retrieval for removing a vector unit in the vector unit specification program in step S18. Normally, a DNA strand can be cleaved using restriction enzymes different between the vector side and DNA fragment side. In this example, however, it is assumed that the same restriction enzyme is used for both vector and DNA fragment sides. That is, according to the present embodiment, HIND III is used as the restriction enzyme on the 5' sides of the vector and DNA fragment, while XBA I is used as the restriction enzyme on the 3' sides of the vector and DNA fragment. As shown in FIG. 2, the base sequence at the binding point between the vector and the DNA fragment is the same as the base sequence of the restriction enzyme site.

FIG. 12 is a flowchart showing the vector unit specification and deleting program in step S18 shown FIG. 7. This process include steps S21 through S25.

First, the base sequence of the retrieval key is determined in step S21. Based on the type of vector and the data about the restriction enzymes, two retrieval keys on the 5' and 3' ends, that is, the forward and backward retrieval keys, are generated. In step S22, a homology retrieval is performed using the forward and backward retrieval keys. Thus, a list of primary candidates for a boundary portion representing the boundary between the vector and DNA fragment on the 5' and 3' sides is generated. There can be a plurality of primary candidates for the boundary portion on both 5' and 3' sides.

In step S23, a list of secondary candidates for the boundary portion is generated. That is, a homology check is made between the primary candidate for a boundary on the 5' side and its forward area (the preceding area) and the primary candidate for a boundary on the 3' side and its backward area (the following area), and the multiple cloning site. Thus, the secondary candidate for a boundary portion can be obtained. In step S24, it is checked that the secondary candidate for each boundary portion is unique (only one), and the relationship in position is checked between the secondary candidates on the 5' and 3' sides. If the relationship in position is consistent, then the secondary candidate for the boundary portion is determined as a cleaved portion in step S25, thereby terminating the process.

FIGS. 13A through 13C show the restriction enzyme site and the area in the restriction enzyme site after the cleaving process. The restriction enzyme site is not always cleaved at the same points in the double-stranded. That is, there can be the following cases:

(1) A single-stranded area is found on the 3' side as shown in FIG. 13A;
(2) A single-stranded area is found on the 5' side as shown in FIG. 13C;
(3) Double strands are cleaved at the same points as shown in FIG. 13B.

In this example, the term "the single-stranded area is found on the 3' side" means that the area B3 which becomes a single-strand remains on the 3' side after the cleaving process shown in FIG. 13A. Likewise, the term "the single-stranded area is found on the 5' side" means that the area B5 which becomes a single-strand remains on the 5' side after the cleaving process shown in FIG. 13C. The 3' and 5' sides refer to the position of the strand A.

In FIGS. 13A through 13C, the portion remaining in the double-stranded state on the 5' side in the restriction enzyme site is referred to as an area A (the same for strand B). Likewise, the portion remaining in the double-stranded state on the 3' side in the restriction enzyme site is referred to as an area C. The portion provided on the 5' side as a single strand is referred to as an area B5. The portion provided on the 3' side as a single strand is referred to as an area B3. Even if the vector and the object DNA fragments are cleaved using different restriction enzymes, the vector can be bound to the object DNA fragments if the base sequences match in the area B. FIGS. 13A through 13C indicate the restriction enzyme site before the cleaving process.

The restriction enzyme site and the cleaving operation are described further in detail by referring to a practical example. As described above, the double stranded DNA is represented by a single strand A as follows. "^" indicates a cleaving point).

The representation "ACTA^GT" indicates that the strands A and B are cleaved as follows.

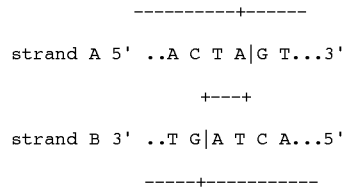

This corresponds to the case shown in FIG. 13C where AC indicates area A, TA indicates area B5, GT indicates area C.

Similarly, "A^CTAGT" indicates the following cleaving form.

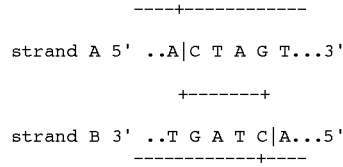

This corresponds to the case shown in FIG. 13A where A indicates area A, CTAG indicates area B3, T indicates area C.

When the object DNA fragments are integrated into the vector, a total of four restriction enzyme sites, that is, the portions before and after the portions of the object DNA fragments cleaved when the object DNA fragments are generated and the portions before and after the cleaved portions of the vector are used. Normally, the restriction enzymes for the above described four cleaved portions are selected independently. If a portion provided with a cleaved single-stranded area equals a base sequence in a single-stranded area to be bound correspondingly, then the ends of the two fragments can be bound to each other.

For example, between ACTA^GT and TGTA^CA, each of the single-stranded areas is provided on the 5' side, the base sequence of the single-stranded area equals "TA", and they can be bound to each other.

On the other hand, between ACTA^GT and TG^TACA, each of the single-stranded areas is provided on the 5' side as in the above mentioned case, but they have the single-stranded areas in different positions, and therefore the fragment ends cannot be bound to each other.

FIG. 14 shows the junction of the restriction enzyme sites in which the vector and the object DNA fragments are bound to each other. In FIG. 14, the vector 5' side is referred to as V1, the vector 3' side is referred to as V2, the object DNA fragment 5' side is referred to as F1, and the object DNA fragment 3' side is referred to as F2. For example, the A area of the restriction enzyme site of the cleaved portion on the vector 5' side is represented by "V1A".

With this representation, the sequence of the junction on the 5' side in the base sequences of the junction can be [V1A]+[V1B5]+[F1C] if a single-stranded area exists on the vector side, [V1A]+[F1C] if no single-stranded area exists, and [V1A]+[F1B3]+[F1C] if the single-stranded area is located on one end of the object DNA fragment. The sequence of the junction on the 3' side in the base sequences of the junction can be [F2A]+[F2B5]+[V2C] if a single-stranded area exists on the object DNA fragment side, [F2A]+[V2C] if no single-stranded area exists, and [F2A]+[V2B3]+[V2C] if the single-stranded area is located on the vector side.

According to the present embodiment, the base sequence of the 5' side junction and the base sequence of the 3' side junction are used as a 5' side (forward) retrieval key and a 3' side (backward) retrieval key respectively.

Figure 15:
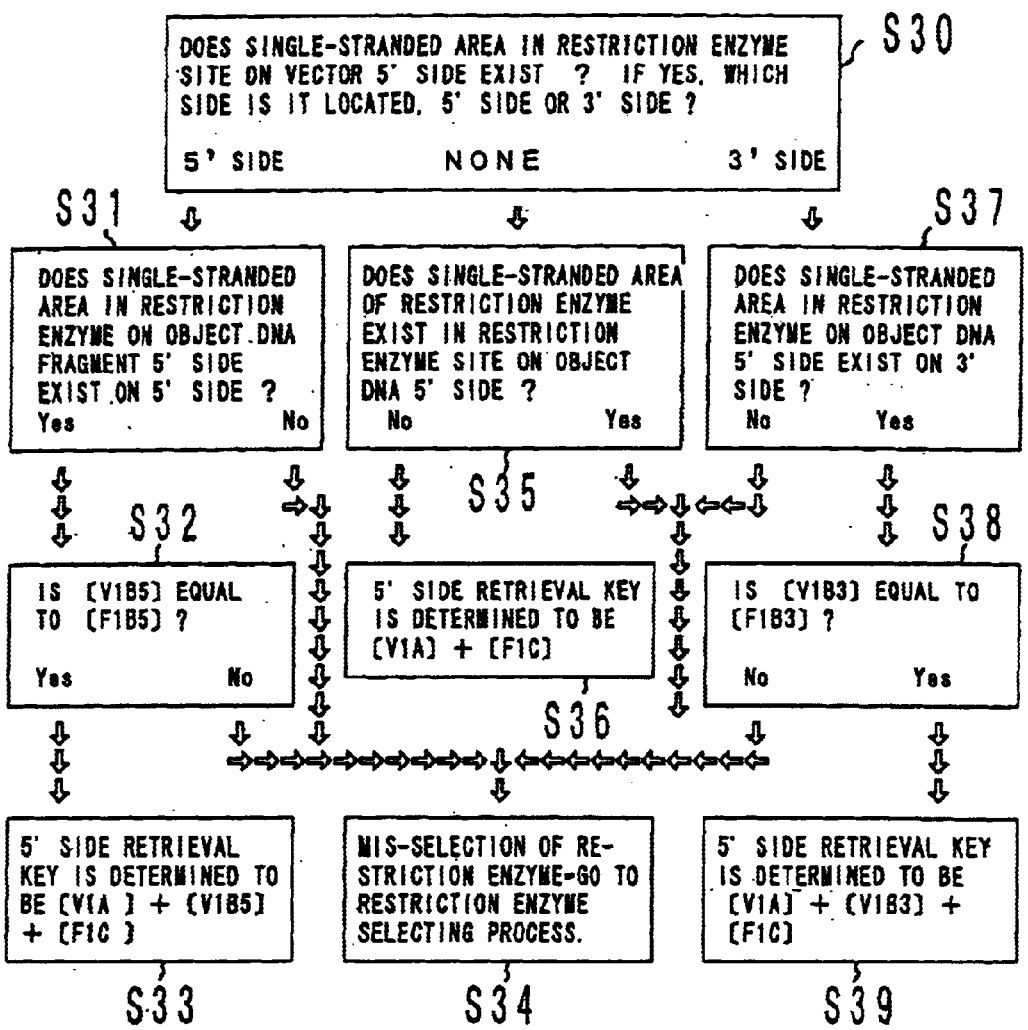
FIG. 15 is a flowchart showing the 5' side retrieval key determining process.

FIG. 15 is a flowchart showing the 5' side retrieval key determining process. When the process is started as shown in FIG. 15, it is determined in step S30 whether or not a single-stranded area of the restriction enzyme site on the vector 5' side exists. If it exists, it is further determined whether the single-stranded area is located on the 5' or 3' side. If it is located on the 5' side, it is determined in step S31 whether or not the single-stranded area of the restriction enzyme site on the object DNA fragment 5' side is located on the 5' side. If it exists there (yes in S31), it is further determined in step S32 whether or not the base sequences [V1B5] and [F1B5] in respective single-stranded areas match each other (when read from the 5' side). If they match (yes in S32), then the cleaved portions can be joined. In step S33, the 5' side retrieval key is defined as [V1A]+[V1B5]+[F1C], thereby terminating the process.

If it is determined in step S31 that the single-stranded area on the object DNA fragment 5' side is not located on the 5' side (no in S31), and if it is determined in step S32 that the base sequences of the single-stranded area do not match each other even if the single-stranded area exists (no in S32), then it is determined in step S34 that the restriction enzyme has been mistakenly selected, and control is returned to the restriction enzyme selecting process, thereby repeating the process.

If it is determined in step S30 that no single-stranded area exists on the vector 5' side, it is further determined in step S35 whether or not a single-stranded area exists in the restriction enzyme site on the object DNA fragment 5' side. If not (no in S35), the retrieval key on the 5' side is defined as [V1A]+[F1C] in step S36, and the process terminates. If it is determined in step S35 that the single-stranded area exists for the object DNA fragment (yes in S35), then it is determined in step S34 that the restriction enzyme has been mistakenly selected, and control is returned to the restriction enzyme selecting process.

If it is determined in step S30 that the single-stranded area to be located on the vector 5' side actually exists on the 3' side, then it is determined in step S37 whether or not the single-stranded area in the restriction enzyme site to be located on the object DNA fragment 5' side really exists on the 3' side. If yes in step S37, it is determined in step S38 whether or not the base sequence [V1B3] equals [F1B3] in the single-stranded area. If yes in step S38, the retrieval key on the 5' side is defined in step S39 as [V1A]+[V1B3]+[F1C] and the process terminates. On the other hand, if the single-stranded area does not exist on the 3' side in step S37 (no in S37), or if it actually exists there but it is determined in step S38 that the two sequences in the single-stranded area are not equal to each other (no in S38), then it is determined in step S34 that the restriction enzyme has been mistakenly selected, and control is returned to the restriction enzyme selecting process.

Figure 16:
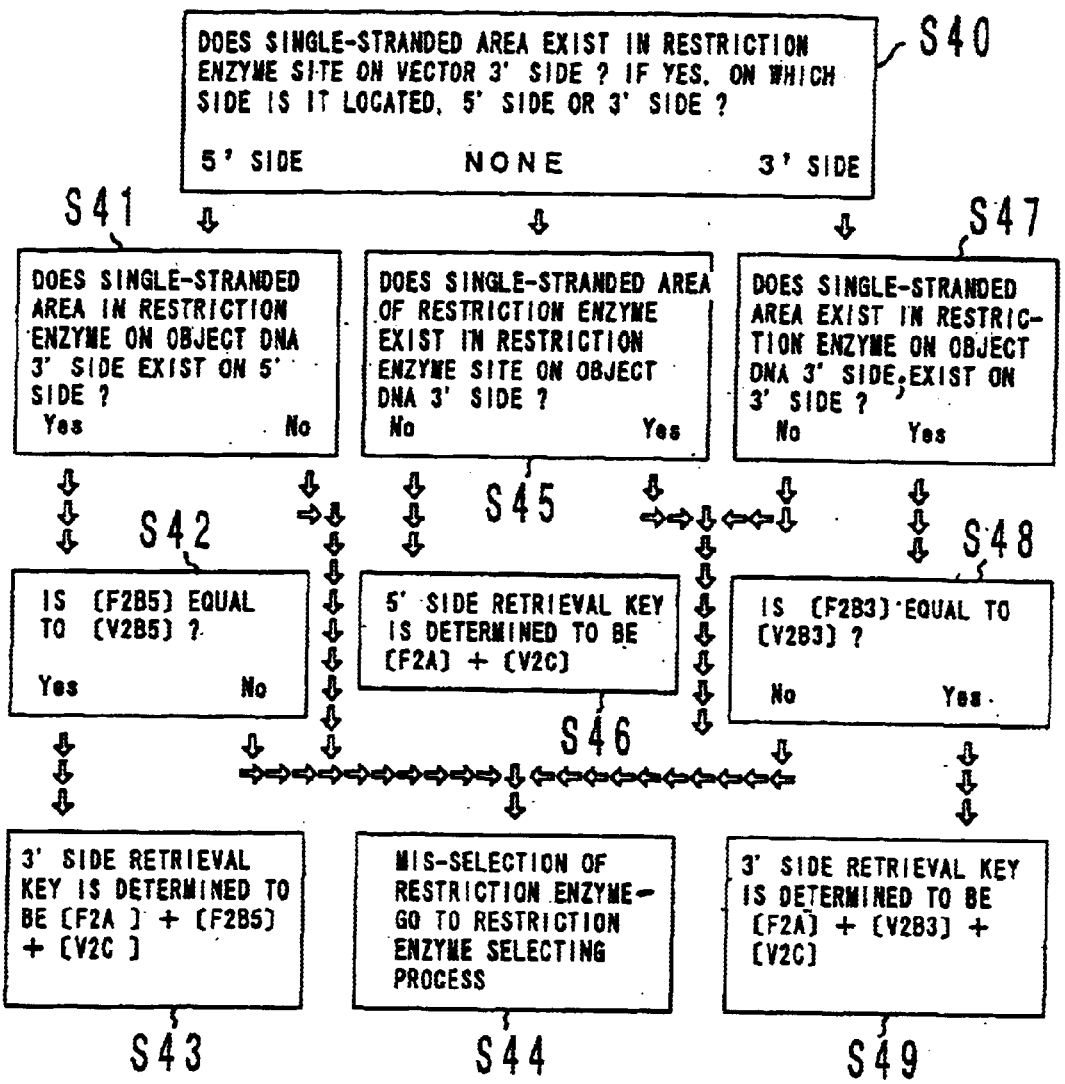
FIG. 16 is a flowchart showing the 3' side retrieval key determining process.

FIG. 16 is a flowchart showing the process of determining the retrieval key on the 3' side. Since the flowchart is almost the same as that for the 3' side as shown in FIG. 15, the detailed explanation is omitted here. Steps S40 through S49 shown in FIG. 16 correspond to steps S30 through S39 in FIG. 13. If the single-stranded areas of the restriction enzyme sites to be located on the vector 3' side and object DNA fragment 3' side are actually located on the 5' side, then [F2A]+[F2B5]+[V2C] is defined as the retrieval key on the 3' side. If the single-stranded areas on the 3' side do not exist, then [F2A]+[V2C3] is defined as the retrieval key on the 3' side. If the single-stranded areas exist on the 3' side, then [F2A]+[V2B3]+[V2C] is defined as the retrieval key on the 3' side.

The vector unit specification program in the present embodiment is described as follows by referring to practical examples. FIG. 17 describes the forward retrieval key and backward retrieval key according to the present embodiment. In this example, an object DNA fragment is incorporated into the multiple cloning site of the vector PUC18 described by referring to FIG. 10. That is, it is assumed that the HIND III is used as the restriction enzyme on the 5' sides of the vector and object DNA fragment, and that the XBA I is used as the restriction enzyme on the 3' sides of the vector and object DNA fragment. In this case, the base sequence depending on the restriction enzyme site at the junction between the vector and object DNA is the same as the base sequence in the restriction enzyme site as shown in FIG. 17. Therefore, the forward retrieval key, that is, the retrieval key on the 5' side, is equal to the base sequence of the restriction enzyme site HIND III, and the backward retrieval key, that is, the retrieval key on the 3' side, is equal to the base sequence of the restriction enzyme site XBA I. In the multiple cloning site shown in FIG. 10, the portion other than the area replaced with the object DNA fragment is referred to as the residual multiple cloning site according to the present embodiment.

Figure 18:
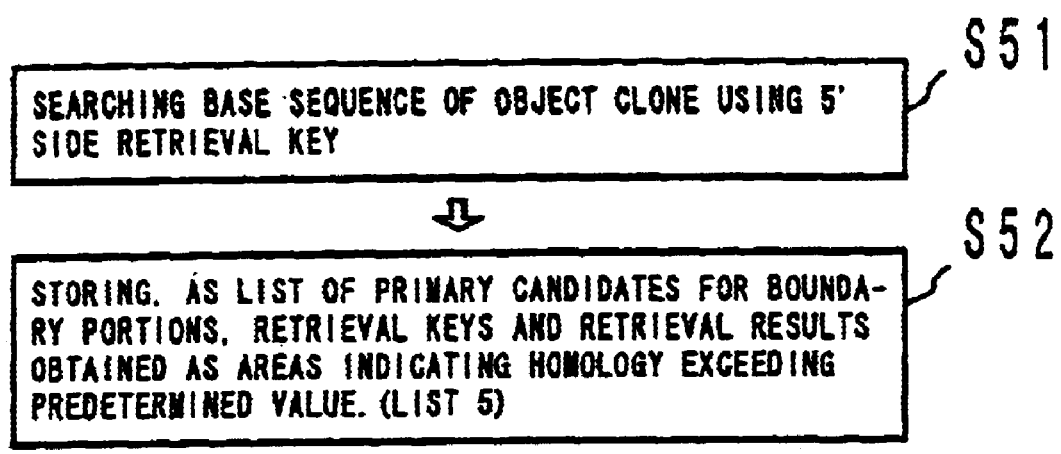
FIG. 18 is a flowchart showing the process of retrieving a primary candidate for the 5' side boundary portion.

FIG. 18 is a flowchart showing the process of retrieving the primary candidate for the boundary on the 5' side using the 5' side retrieval key shown in FIG. 17. When the process starts as shown in FIG. 18, the homology retrieval is performed in the base sequence of the object clone using the 5' side retrieval key in stop S51. The retrieval keys and retrieval results obtained as areas indicating a homology exceeding a predetermined value (the number of bases matching in, for example, 6 bases) are listed as primary candidates for boundary portions in step S52, then terminating the process.

Figure 19:
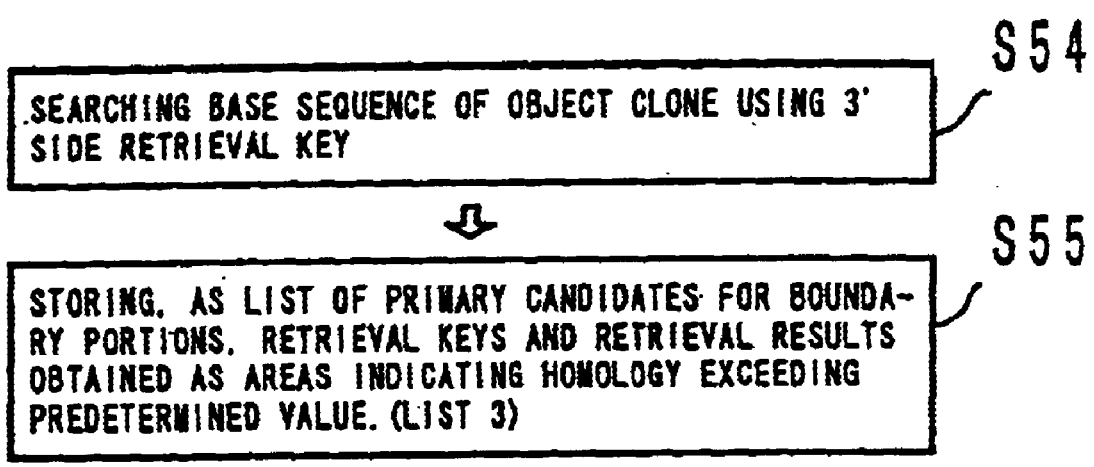
FIG. 19 is a flowchart showing the process of retrieving a primary candidate for the 3' side boundary portion.

FIG. 19 is a flowchart showing the process of retrieving the primary candidate for the boundary on the 3' side. The retrieval process is almost the same as the retrieval process shown in FIG. 18. Steps S54 and S55 correspond to steps S51 and S52 shown in FIG. 18. The process is different from that shown in FIG. 18 in that retrieval uses the backward retrieval key, that is, the 3' side retrieval key, to produce a list of the primary candidates for the boundary on the 3' side.

FIG. 20 is a flowchart showing the process of retrieving the secondary candidates by selecting secondary candidates from the primary candidates for the boundary portion obtained as shown in FIG. 18, that is, normally from a plurality of primary candidates. Of the restriction enzyme site used in cleaving the 5' side of the multiple cloning site of the vector, the area to the 5' side of the restriction enzyme site is defined in step S61 as the 5' side residual multiple cloning site 5MCS when the process starts as shown in FIG. 20. In FIG. 17, the 5MCS is the same as the 5' side retrieval key.

Then, in step S62, when the vector data base includes base sequences outside the multiple cloning site, a sequence containing the base sequence and the 5' side residual multiple cloning site 5MCS is defined as a side residual vector area 5VA. That is, when five base sequences are included to the 5' side of the 5' side retrieval key as shown in FIG. 17 (in this example, to the 5' side of the 5' side residual multiple cloning site), the five bases to the 5' side of the 5MCS are added to the 5MCS in defining the 5' side residual vector area 5VA in step S62. In FIG. 17, the 5VA is the base sequence GTGCCAAGCTT (SEQUENCE ID NO. 4). If only the base sequence in the multiple cloning site is included in the vector data base, then the 5VA is assumed to equal the 5MCS However, since the data base normally includes the base sequences before and after the multiple cloning site, the homology check is effective as described below.

After the 5' side residual vector area 5VA has been obtained, the processes in steps S63 through S66 are performed on all elements in the list of the primary candidates for the boundary portion as shown in FIG. 18, and the homology check is then made. First, in step S63, the area of the DNA base sequence to the 5' side of each candidate, including each of the primary candidates (LIST5) for the boundary portion, is defined as the homology check area 5HCA for the candidate. In step S64, the number of bases of the 5VA, the number of bases of the 5HCA, and a predetermined value (the number 20 in this example) are compared with each other. The smallest of the three numbers is obtained as the number of bases HCB for use in the homology check. In step S65, the number of bases equal to the number of HCBs are retrieved on the 3' side of the 5VA and checked in the homology check in comparison with the same number of bases on the 3' side of the 5HCA. If the homology check indicates a value larger than a predetermined value, then the same number of bases as the HCBs on the DNA base sequence side are defined as the secondary candidates for the 5' side boundary portion in step S66, thereby terminating the process. The predetermined number 20, which is used in comparing for obtaining the HCBs, indicates an appropriate constant, but the value itself does not have a special meaning.

Figure 21:
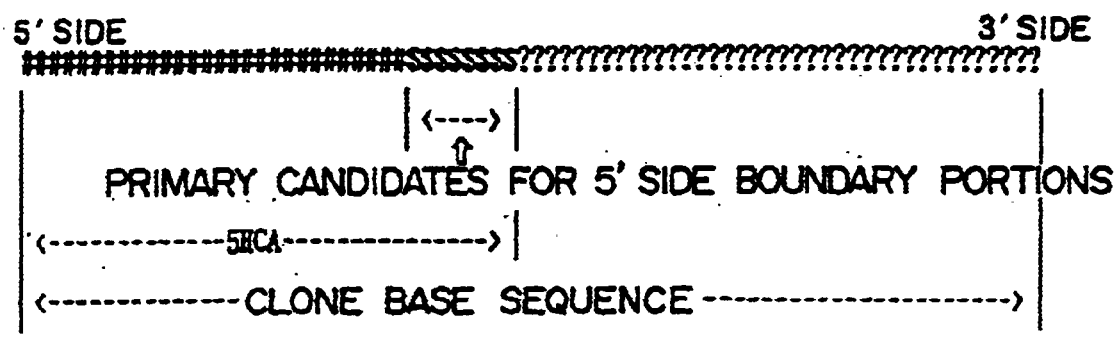
FIG. 21 shows the homology check on the primary candidate for the 5' side boundary portion.

FIG. 21 shows the homology check for use as a process of retrieving the secondary candidates for the boundary portion on the 5' side. In FIG. 21, the area to the 5' side of the clone base sequence, including the primary candidates for the 5' side boundary portion, is defined as the area 5HCA to be processed in the homology check. From the area 5HCA, the number of bases in the HCB equal to the number of bases in the 5VA are retrieved to be processed in the homology check. Thus, the secondary candidates for the boundary portion are determined.

Figure 23:
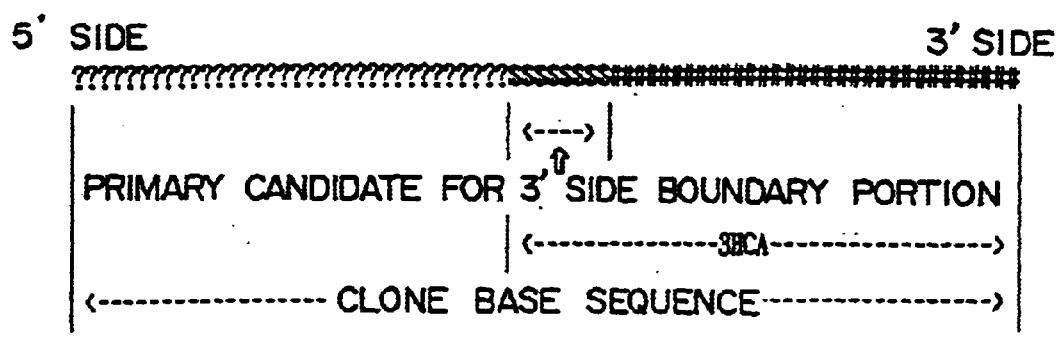
FIG. 23 shows the homology check on the primary candidate for the 3' side boundary portion.

FIG. 22 is a flowchart showing the process of determining the secondary candidates for the boundary portion on the 3' side. FIG. 23 shows the secondary candidate retrieval process on the 3' side. These processes are almost the same as those shown in FIGS. 20 and 21 and the detailed explanation is omitted here.

Figure 24:
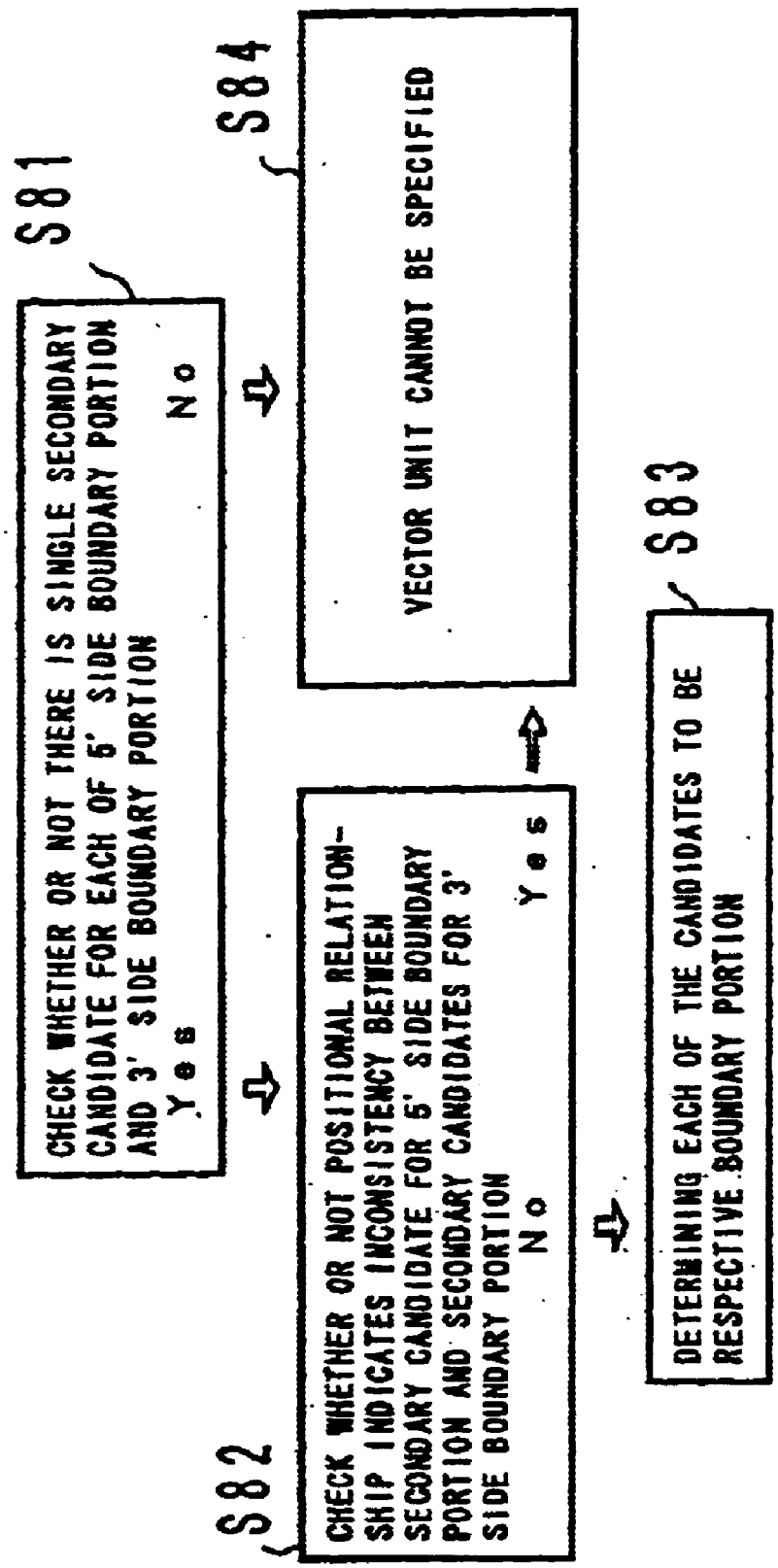
FIG. 24 is a flowchart showing the process of determining a cleaved portion to remove a vector unit.

FIG. 24 is a flowchart showing the process of determining the finally cleaved portion to remove the vector unit. When the process starts as shown in FIG. 24, it is determined in step S81 whether or not one secondary candidate is specified for each of the boundary portions on the 5' and 3' sides. If yes, it is determined in step S82 whether or not the secondary candidates for the 5' and 3' sides are inconsistent in position to each other, that is, whether or not the secondary candidate on the 3' side comes before the secondary candidate on the 5' side. It is further determined whether or not the two secondary candidates overlap each other. Unless the secondary candidates are inconsistent, they are determined to be cleaved portions, thereby terminating the process in step S83.

On the other hand, unless there is a single secondary candidate on each of the 5' and 3' sides in step S81, or if the positions of the two secondary candidates indicate inconsistency in step S82, then it is determined in step S84 that the vector unit cannot be specified and the process terminates.

If the cleaved portions are thus determined, a vector unit removing program in step S18 shown in FIG. 7 is executed. The vector unit removing program removes the vector unit including the cleaved portion determined in FIG. 24. That is, the 5' side base sequence including the secondary candidate for the 5' side boundary portion determined to be a cleaved portion, and the 3' side base sequence including the secondary candidate for the 3' side boundary portion, are removed as a vector unit.

The vector unit can also be removed from the cleaved portion through the restriction enzyme in the restriction enzyme site, not completely cleaved as a cleaved portion, that is, the entire unit including all base sequences in the restriction enzyme site. Practical embodiments of the present invention are not limited to the above described applications.

Various retrieval results such as boundary portion primary candidate retrieval results, boundary portion secondary candidate retrieval results, etc. can be identified on the display unit. A vector unit to be deleted can also be easily identified.

Figure 25:
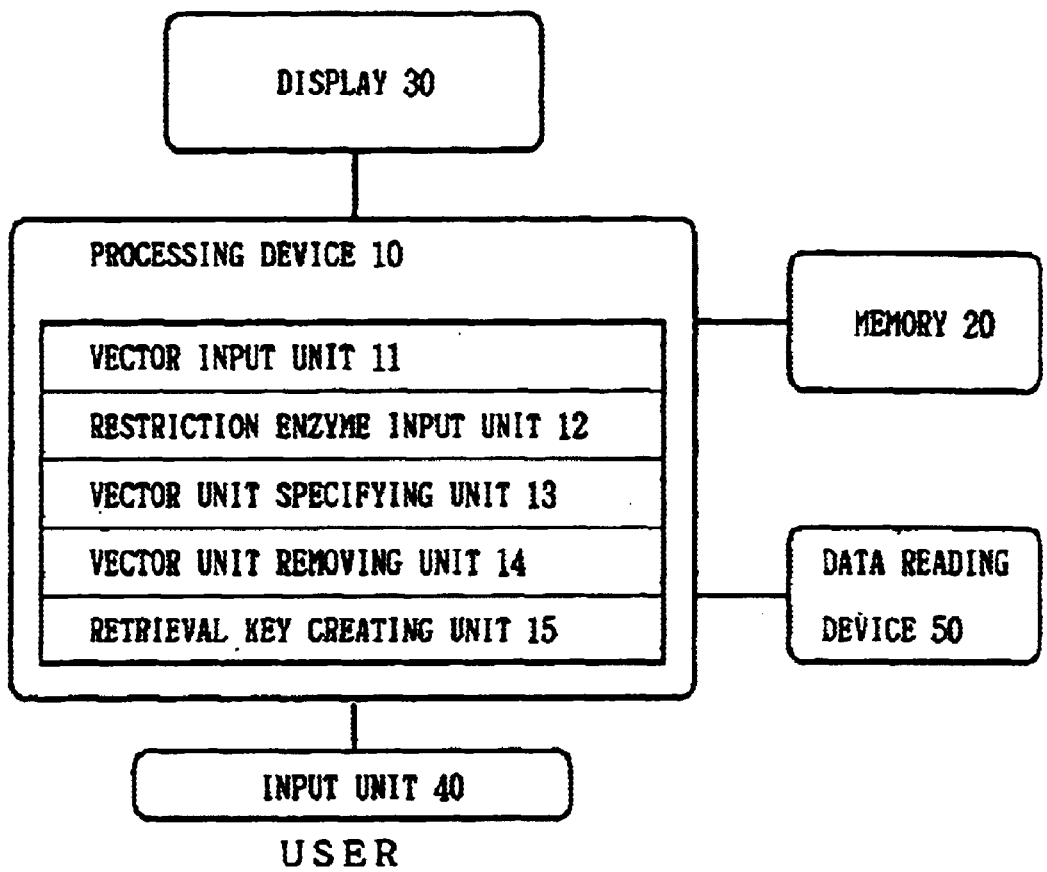
FIG. 25 shows a configuration of a vector unit removing device according to the invention.

The methods and processes described above can be realized using an automatic control device such as a computer. As shown in FIG. 25, the control device according to the invention includes a processing device 10, memory 20, display 30, input unit 40, and data reading device 50.

The processing device 10 includes a vector input unit 11 which performs the vector input process of step S6 in FIG. 6, restriction enzyme input unit 12 which performs the restriction enzyme input process of step S7, vector unit specifying unit 13 which performs the vector unit specification process of step S8, vector unit removing unit 14 which performs the vector unit removing process of step S9. The processing device 10 may further include a retrieval key creating unit 15 which performs the retrieval key creating process in step S8 (step S21 in FIG. 12) independently.

The memory 20 stores the vector list including the names of the vectors used in step S13 in FIG. 7 and the corresponding information, and the restriction enzyme list including the names of the restriction enzymes used in steps S14 through S17 and the corresponding information. The memory 20 may further store the programs used for realizing the above described methods and processes which include the retrieval key creating program, the vector unit specification program, vector unit removal program, etc. A hard disk, RAM, ROM, or other types of information storage unit can be used for the memory 20.

The display 30 displays the above described programs and lists. The user inputs commands and the information necessary for selecting the programs, vectors, and restriction enzymes, and for performing the programs according to the contents indicated on the display 30, through the input unit 40.

The data reading device 50 reads data stored in a storage medium, which are used for performing the methods and processes and including the above described lists and programs, to inform the processing device 10. A magnetic disk, an optical disk, an optical-magnetic disk, or other types of storage mediums can be used for the storage medium.

As described above in detail, normally a plurality of primary candidates for a boundary portion can be obtained by performing the homology retrieval using as a retrieval key a very short base sequence at the boundary portion between the vector unit and the object DNA fragment, and a further homology check is made on the primary candidate to correctly specify a vector unit according to the present invention. If a sequencing operation is mistakenly performed on the 3' end side when the sequencer outputs data, the present invention successfully removes a vector unit on the 3' end side. Furthermore, the user can also remove the portion not automatically removed according to the prior art technologies by displaying the retrieval results as separable units on the display unit. Thus, the vector unit can be retrieved with precision in a short time.

What is claimed is:

1. A method for analyzing base sequence date and removing, based on said data, a vector base sequence from a recombinant DNA base sequence, comprising:

storing data identifying each of restriction enzymes and data of base sequences at a plurality of restriction enzyme sites of a plurality of vectors correspondingly, in a database;

searching base sequence data of a recombinant DNA obtained by splicing an object DNA fragment into a vector;

obtaining the base sequence data at a front restriction enzyme site and the base sequence data at a back restriction enzyme site, as specified by corresponding to a restriction enzyme used for cleaving the vector and a restriction enzyme used for obtaining the object DNA fragment, from the database;

generating a first forward retrieval key using the obtained base sequence data of the front restriction enzyme site and a first backward retrieval key using the obtained base sequence data of the back restriction enzyme site;

retrieving base sequence date of the recombinant DNA obtained by a search using the first forward and first backward retrieval keys, and specifying a junction between the vector and the object DNA fragment;

removing the vector base sequence at the specified junction, wherein sequence data of the first forward retrieval key and of the first backward retrieval key are generated by base sequence data of the vector entered in a vector database, data of a multiple cloning site in the vector, and data of a restriction enzyme site in the multiple cloning site, wherein data of a forward base sequence from a cleaving point in the restriction enzyme site in the multiple cloning site of the vector are acquired from the database, and a second forward retrieval key is generated using the acquired forward base sequence data of the cleaving point of the restriction enzyme site of the vector, performing first homology retrieval on condition that a first similarity value between retrieval base sequence data of the recombinant DNA and the first forward and first backward retrieval keys is equal to or larger than a predetermined value, obtaining a candidate for a base sequence at the junction between the vector and the object DNA fragment according to a result of the first homology retrieval, and performing a second homology retrieval on condition that a second similarity value between base sequence data of a plurality of first candidates for the junction, and base sequence data of the second forward retrieval key, is equal to or larger than a predetermined value.

2. A method for analyzing base sequence data and removing, based on said data, a vector base sequence from a recombinant DNA base sequence, comprising:

storing data identifying each of restriction enzymes and data of base sequences at a plurality of restriction enzyme sites of a plurality of vectors correspondingly, in a database;

searching base sequence data of a recombinant DNA obtained by splicing an object DNA fragment into a vector;

obtaining the base sequence data at a front restriction enzyme site and the base sequence data at a back restriction enzyme site, as specified by corresponding to a restriction enzyme used for cleaving the vector and a restriction enzyme used for obtaining the object DNA fragment, from the database;

generating a first forward retrieval key using the obtained base sequence data of the front restriction enzyme site and a first backward retrieval key using the obtained base sequence data of the back restriction enzyme site;

retrieving base sequence data of the recombinant DNA obtained by a search using the first forward and first backward retrieval keys, and specifying a junction between the vector and the object DNA fragment;

removing the vector base sequence at the specified junction, wherein the sequence data of the first forward retrieval key and of the first backward retrieval key are generated by base sequence data of the vector entered in a vector database, data of a multiple cloning site in the vector, and data of a restriction enzyme site in the multiple cloning site, wherein forward base sequence data of a forward cleaving point of the restriction enzyme site of the vector, and backward base sequence data of a backward cleaving point of the vector are acquired from the database, and a second forward retrieval key and a second backward retrieval key are generated using the base sequence data of the acquired forward and backward base sequence data of the cleaving points, respectively, performing a first homology retrieval on condition that a first similarity value between retrieval base sequence data of the recombinant DNA and the first forward and first backward retrieval keys is equal to or larger than a predetermined value, obtaining a candidate for a base sequence at the junction between the vector and the object DNA fragment according to a result of the first homology retrieval, and performing a second homology retrieval on condition that a second similarity value between base sequence data of a plurality of first candidates for the junction, and base sequence data of the second forward retrieval key, is equal to or larger than a predetermined value.

3. The method according to claim 2, wherein the sequence data of the first forward and first backward retrieval keys are generated by base sequence data of the vector entered in a vector database, data of a multiple cloning site in the vector, and data of a restriction enzyme site in the multiple cloning site, and wherein the second homology retrieval is performed using both the second forward and second backward retrieval keys.

4. The method according to claim 2, further comprising:

obtaining, as a forward vector unit candidate for the vector base sequence, a forward base sequence selected by the second homology retrieval, and a base sequence before said forward base sequence; and obtaining, as a backward vector unit candidate for the vector base sequence, a backward base sequence selected by the second homology retrieval, and a base sequence after said backward base sequence.

5. The method according to claim 4, wherein said forward vector unit candidate and said backward vector unit candidate are removed from the recombinant DNA base sequence, when there is only one candidate respectively for the specified forward and backward base sequences, and the specified forward and backward base sequences do not overlap each other.

6. A method for analyzing base sequence data and removing, based on said data, a vector base sequence from a recombinant DNA base sequence, comprising:

storing data identifying each of restriction enzymes and data of base sequences at a plurality of restriction enzyme sites of a plurality of vectors correspondingly, in a database;

searching base sequence data of a recombinant DNA obtained by splicing an object DNA fragment into a vector;

obtaining the base sequence data at a front restriction enzyme site and the base sequence data at a back restriction enzyme site, as specified by corresponding to a restriction enzyme used for cleaving the vector and a restriction enzyme used for obtaining the object DNA fragment, from the database;

generating a first forward retrieval key using the obtained base sequence data of the front restriction enzyme site and a first backward retrieval key using the obtained base sequence data of the back restriction enzyme site;

retrieving base sequence data of the recombinant DNA obtained by a search using the first forward and first backward retrieval keys, and specifying a junction between the vector and the object DNA fragment;

removing the vector base sequence at the specified junction, wherein backward base sequence data from a cleaving point in a multiple cloning site of the vector corresponding to the restriction enzyme are acquired from the database, and a second backward retrieval key is generated using the acquired backward base sequence data of the cleaving point, performing a first homology retrieval on condition that a first similarity value between retrieval base sequence data of the recombinant DNA and the first forward and first backward retrieval keys is equal to or larger than a predetermined value;

obtaining a first candidate for a base sequence at a junction between the vector and the object DNA fragment according to a result of the first homology retrieval; and performing a second homology retrieval to identify at least one area in the vector on condition that a second similarity value between base sequence data of a first candidate for the junction, screened by using the first retrieval keys, and base sequence data of the second backward retrieval key is equal to or larger than a predetermined value.

7. The method according to claim 6, wherein said vector base sequence is removed, when only one area is specified by the second homology retrieval.

8. A device for analyzing base sequence data and removing, based on said data, a vector base sequence from a recombinant DNA base sequence, obtained as a result of performing a cloning process by integrating an object DNA fragment into a vector, comprising:

a database storing data identifying each of restriction enzymes, and data of base sequences at a plurality of restriction enzyme sites of a plurality of vectors correspondingly;

an obtaining unit obtaining base sequence data are front restriction enzyme site and base sequence data at a back restriction enzyme site, as specified corresponding to a restriction enzyme used for cleaving the vector and a restriction enzyme used for obtaining the object DNA fragment, from the database;

a generation unit generating a first forward retrieval key using the obtained base sequence data of the front restriction enzyme site, and a first backward retrieval key using the obtained base sequence data of the back restriction enzyme site;

a retrieving unit retrieving base sequence data of the recombinant DNA obtained using the first forward and first backward retrieval keys, and specifying a junction between the vector end the object DNA fragment; and a removal unit for removing the vector base sequence at the specified junction, wherein each of said first forward and first backward retrieval keys includes sequence data including an end portion of the object DNA fragment and sequence data including an end portion of the vector base sequence, and specifies a candidate for the junction between the vector base sequence and the object DNA fragment, wherein a second retrieval key, including sequence data longer than that of said first forward and first backward retrieval keys, is generated, and the junction is specified using the second retrieval key.

9. The device according to claim 8, wherein said object DNA fragment is specified by removing the junction and base sequence distal to the junction and the object DNA fragment from the DNA base sequence.

* * * * *